(12) United States Patent
Wawro et al.

(10) Patent No.: US 12,416,628 B2
(45) Date of Patent: Sep. 16, 2025

(54) PORTABLE PHOTONIC SENSOR SYSTEM AS AN EARLY DETECTION TOOL FOR OVARIAN CANCER

(76) Inventors: Debra Wawro, Paradise, TX (US); Shelby Zimmerman, Arlington, TX (US); Yiwu Ding, Marcellus, NY (US); Robert Magnusson, Arlington, TX (US); Peter Koulen, Leawood, KS (US)

( * ) Notice: Subject to any disclaimer, the term of this patent is extended or adjusted under 35 U.S.C. 154(b) by 0 days.

(21) Appl. No.: 13/470,250

(22) Filed: May 11, 2012

(65) Prior Publication Data
US 2013/0130939 A1 May 23, 2013

Related U.S. Application Data

(60) Provisional application No. 61/485,095, filed on May 11, 2011, provisional application No. 61/487,204, filed on May 17, 2011.

(51) Int. Cl.
*G01N 33/543* (2006.01)
*G01N 27/04* (2006.01)
*G01N 33/574* (2006.01)

(52) U.S. Cl.
CPC ....... *G01N 33/54366* (2013.01); *G01N 27/04* (2013.01); *G01N 33/54373* (2013.01); *G01N 33/57449* (2013.01)

(58) Field of Classification Search
CPC .................. G01N 33/54366; G01N 33/57449
See application file for complete search history.

(56) References Cited

U.S. PATENT DOCUMENTS

| | | | |
|---|---|---|---|
| 7,070,987 B2 * | 7/2006 | Cunningham ..... | G01N 21/7743 436/805 |
| 2003/0124579 A1 * | 7/2003 | Mack et al. | |
| 2005/0095592 A1 * | 5/2005 | Jazaeri ................ | C12Q 1/6886 435/6.16 |
| 2007/0054268 A1 | 3/2007 | Sutherland et al. | |
| 2008/0131885 A1 | 6/2008 | Pratilas et al. | |
| 2008/0286814 A1 * | 11/2008 | Lopez ..................... | C07K 7/08 435/7.1 |
| 2009/0024019 A1 | 1/2009 | Stein et al. | |
| 2009/0068668 A1 | 3/2009 | Duer | |

OTHER PUBLICATIONS

Wawro et al 2009 Proc. SPIE 7173, Optical Fibers and Sensors for Medical Diagnostics and Treatment Applications IX: p. 717303-1 to 717303-9.*

(Continued)

*Primary Examiner* — Christopher L Chin
(74) *Attorney, Agent, or Firm* — Theodore F. Shiells

(57) ABSTRACT

A guided mode resonance (GMR) sensor that can be used to simultaneously detect an array of analytes. It provides a diagnostic system that can rapidly detect an array of biomarker proteins in patient samples (such as blood, serum or plasma for example) which can be used as an accurate means to conduct a differential analysis of proteins that allows the discrimination of early and late stages of disease, such as metastatic versus primary ovarian serous carcinomas. The GMR sensor can be provided in a compact size such that it can be portable.

19 Claims, 26 Drawing Sheets
(26 of 26 Drawing Sheet(s) Filed in Color)

(56) References Cited

OTHER PUBLICATIONS

Wawro et al Feb. 25, 2010 Proc. SPIE 7572, Optical Diagnostics and Sensing X: Toward Point-of-Care Diagnositcs, p. 75720D-1 to 75720D-6.*
Seurynck-Servoss et al 2007 Analytical Biochemistry 371(1): 105-115.*
Magnusson et al. "Resonant Photonic Biosensors with Polarization-Based Multiparametric Discrimination in Each Channel", Sensors 2011, 11, 1476-1488; doi:10.3390/s110201476, published Jan. 26, 2011.*
Kaja et al. "Detection of novel biomarkers for ovarian cancer with an optical nanotechnology detection system enabling label-free diagnostics" Journal of Biomedical Optics 17(8), 081412 (Aug. 2012), pp. 081412-1 to 081412-8.*
Zhang et al. "Three Biomarkers Identified from Serum Proteomic Analysis for the Detection of Early Stage Ovarian Cancer" Cancer Research 64, 5882-5890, 2004.*
Bignotti, Eliana et al. "Gene expression profile of ovarian serous papillary carcinomas: identification of metastasis-associated genes." American journal of obstetrics and gynecology vol. 196,3 (2007): 245.e1-11. doi: 10.1016/j.ajog.2006.10.874 (Year: 2007).*
Bignotti et al Differential gene expression profiles between tumor biopsis and short-term primary cultures 2006 (Year: 2006).*

\* cited by examiner

PORTABLE PHOTONIC SENSOR SYSTEM AS AN EARLY DETECTION TOOL FOR OVARIAN CANCER

PRIORITY

This application claims priority to U.S. provisional patent application Ser. No. 61/485,095, filed May 11, 2011; and Ser. No. 61/487,204, filed May 17, 2011, the contents of which are incorporated by reference herein for all purposes.

UNITED STATES GOVERNMENT INTERESTS

The development of this invention was partially funded by the United States government through a grant for the United States National Institutes of Health, National Institutes of Health/National Cancer Institute grant number R43CA135960. The United States government may have certain rights in this invention.

BACKGROUND OF THE DISCLOSURE

1. Field of the Invention

The present invention relates to guided-mode resonance (GMR) sensor systems, and in particular to a GMR sensor that can be used to simultaneously detect an array of analytes and can provided in a portable configuration.

2. Description of the Related Art

It is known that resonant leaky modes can be induced on dielectric, semiconductor and metallic periodic layers patterned in one or two dimensions. Among potential applications are ultrasensitive biosensors that can be realized in a wide range of geometries and system architectures. In 1992, Magnusson and Wang [1] suggested application of the GMR effect for spectroscopic sensor applications and disclosed GMR filters that were tunable on variation in resonance structure parameters including thickness and refractive index [2]. Tibuleac et al. and Wawro et al. presented GMR biosensor embodiments as well as new possible applications of these sensors when integrated with optical fibers [3,4]. Following this work, Kikuta et al. [5], Cunningham et al. [6,7] and Fang et al. [8,9] also discussed the use of these resonant elements as biosensors.

A great variety of optical sensors for bio- and chemical detection has been reported in the literature. Key label-free sensor technologies include surface-plasmon resonance sensors, MEMS-based sensors, nano-sensors (rods and particles), resonant mirrors, Bragg grating sensors, waveguide sensors, waveguide interferometric sensors, ellipsometry and grating coupled sensors [10-13]. Other methods include immunomagnetic separation, polymerase chain reaction and standard immunoassay approaches that incorporate fluorescent, absorptive, radioactive and luminescent labels [12,13]. Although dramatically different in concept and function, the surface-plasmon resonance (SPR) sensor [10,11] comes closest in features and operation to the GMR sensor applied in this invention. The term surface plasmon (SP) refers to an electromagnetic field charge-density oscillation that can occur at the interface between a conductor and a dielectric (e.g., gold/glass interface). An SP mode can be resonantly excited by TM-polarized incident light but not TE-polarized light. Phase matching occurs by employing a metallized diffraction grating or by using total internal reflection from a high-index material such as in prism coupling or from a guided wave in an optical fiber. When an SPR surface wave is excited, an absorption minimum occurs in a specific wavelength band. While angular and spectral sensitivity is very high for SPR sensors, the resonance linewidth is rather large. Since typically only a single polarization (TM) can physically be used for detection, changes in refractive index and biolayer attachments cannot simultaneously be resolved in one measurement. This is a particularly significant problem in portable diagnostic applications where thermal variations are probable.

Standard immunoassay tests (such as ELISA and Western blot) involve extensive and complicated incubation and washing steps. In this approach, results are not obtained until 4-24 hours after starting the test.

The absence of reproducible and definitive tools for early detection of cancer greatly increases the occurrence of advanced metastatic forms, with a very high recurrence rate after treatment. However, a differential analysis and diagnosis has the potential to provide the foundation for a significantly refined therapeutic management and for more targeted therapy development of carcinomas.

OBJECTS OF THE INVENTION

It is an object of the present invention to provide a GMR sensor that can be used to simultaneously detect an array of analytes.

It is a further object of the present invention to provide a GMR sensor in a compact size such that can be portable.

It is a further object of the invention to provide a diagnostic system that can rapidly detect an array of biomarker proteins in patient samples (such as blood, serum or plasma for example) which can be used as an accurate means to conduct a differential analysis of proteins that allows the discrimination of early and late stages of disease, such as metastatic versus primary ovarian serous carcinomas.

SUMMARY OF THE INVENTION

In accordance with an embodiment of the invention, a biomarker sensor is provided comprising GMR sensor assembly comprising: a waveguide structure configured for operation at or near one or more leaky modes; means for receiving input light from a source of light that includes one or more line focusing elements to focus input light onto the waveguide structure to cause one or more leaky TE and TM resonant modes; means for the detecting presence of a biomarker indicative of a disease state that may be present in a media in contact with said waveguide structure, comprising means for detecting changes in one or more of the angle, phase, waveshape and/or magnitude of each of a TE resonance and/or a TM resonance to permit distinguishing between first and second physical states of said waveguide structure or its immediate environment, said immediate environment including said media.

In an aspect of this embodiment, the source of light comprises multiple sources of light having distinct wavelengths.

In an embodiment of the invention, a measurement system for detecting the presence of an array of ovarian cancer biomarker proteins in a sample is provided, the array of biomarker proteins including at least three proteins taken from the group: Fibronectin, Apolipoprotein A-I, Calreticulin, Complement C7, Collagen Type I, MAP Kinase 13, TIMP 3, and Ryanodine receptor.

In an aspect of measurement system for detecting the presence of an array of ovarian cancer biomarker proteins, the Ryanodine receptor is Ryanodine receptor 2 and/or Ryanodine receptor 3.

In another aspect of the measurement system for detecting the presence of an array of ovarian cancer biomarker proteins, the array includes other biomarker proteins relevant in ovarian cancer.

In another aspect of the measurement system for detecting the presence of an array of ovarian cancer biomarker proteins, the system is used to determine the stage of ovarian cancer In another aspect of the measurement system for detecting the presence of an array of ovarian cancer biomarker proteins, the system is used to monitor ovarian cancer treatment efficacy.

In another aspect of the measurement system for detecting the presence of an array of ovarian cancer biomarker proteins, the system is used to determine appropriate ovarian cancer treatment modalities.

In another aspect of the measurement system for detecting the presence of an array of ovarian cancer biomarker proteins, the system incorporates biologically selective agents which are selected from a group of antibodies, aptamers, peptides, DNA/RNA, or other agents designed to be selective for biomarker proteins.

In another aspect of the measurement system for detecting the presence of an array of ovarian cancer biomarker proteins, the sample is selected from a group of: serum, blood, urine or other biological fluids.

In another aspect of the measurement system for detecting the presence of an array of ovarian cancer biomarker proteins, the system utilizes a guided-mode resonance waveguide grating to detect the presence of the array of ovarian cancer biomarker proteins.

In an embodiment, a GMR biosensor for detecting the presence of an array of ovarian cancer biomarker proteins in a sample is provided, the array of biomarker proteins including at least three proteins taken from the group: Fibronectin, Apolipoprotein A-I, Calreticulin, Complement C7, Collagen Type I, MAP Kinase 13, TIMP 3, and Ryanodine receptor, said GMR biosensor comprising a waveguide structure configured for operation at or near one or more leaky modes; means for receiving input light from a source of light that includes one or more line focusing elements to focus input light onto the waveguide structure to cause one or more leaky TE and TM resonant modes; means for the detecting presence of a biomarker indicative of a disease state that may be present in a media in contact with said waveguide structure, comprising means for detecting changes in one or more of the angle, phase, waveshape and/or magnitude of each of a TE resonance and/or a TM resonance to permit distinguishing between first and second physical states of said waveguide structure or its immediate environment, said immediate environment including said media.

In an aspect of the GMR biosensor for detecting the array of biomarker proteins, the Ryanodine receptor is Ryanodine receptor 2 and/or Ryanodine receptor 3.

In an aspect of the GMR biosensor for detecting the array of biomarker proteins, the biosensor all detects other biomarker proteins relevant in ovarian cancer.

In an aspect of the GMR biosensor for detecting the array of biomarker proteins, the system is used to determine the stage of ovarian cancer In an aspect of the GMR biosensor for detecting the array of biomarker proteins, the system is used to monitor ovarian cancer treatment efficacy.

In an aspect of the GMR biosensor for detecting the array of biomarker proteins, the system is used to determine appropriate ovarian cancer treatment modalities.

In an aspect of the GMR biosensor for detecting the array of biomarker proteins, the system incorporates biologically selective agents which are selected from a group of antibodies, aptamers, peptides, DNA/RNA, or other agents designed to be selective for biomarker proteins.

In an aspect of the GMR biosensor for detecting the array of biomarker proteins, the sample is selected from a group of: serum, blood, urine or other biological fluids.

In an aspect of the GMR biosensor for detecting the array of biomarker proteins, the system utilizes a guided-mode resonance waveguide grating to detect the presence of the array of ovarian cancer biomarker proteins.

By using GMR sensor technology of the present invention, real-time results can be obtained with no required washing steps. Results can typically be obtained in less than 15 minutes (limited only by the binding dynamics of the ligand-receptor interactions). This greatly simplifies medical diagnostic testing approaches, and will enable personnel in doctor offices and in hospitals to perform routine screening on a much larger scale with dramatically less labor than in current practice.

The present invention further enables differential analysis of proteins that allow the discrimination of early and late stages of ovarian serous carcinomas [14-15]. To this end specialized reagents that allow identification and quantification of such differential diagnostic phenotypes will be employed and combined with technology development thus providing the unequivocal quantitative assessments needed for reliable screening tests.

BRIEF DESCRIPTION OF THE FIGURES

The patent or application file contains at least one drawing executed in color. Copies of this patent or patent application with publication with color drawing(s) will be provided by the Office upon request and payment of the necessary fee.

The following drawings form part of the present specification and are included to further demonstrate certain aspects of the present invention wherein.

DETAILED DESCRIPTION OF EXEMPLARY EMBODIMENTS

Turning now to the figures, tables and further explanation herein, in an embodiment of the invention describes a new sensor system that can provide near-instantaneous detection of biomarker proteins in patient samples (such as blood, serum or plasma for example). This can be used as an accurate means to conduct a differential analysis of proteins that allows the discrimination of early and late stages of disease, such as metastatic versus primary ovarian serous carcinomas [14-15]. To this end, specialized reagents that allow identification and quantification of such differential diagnostic phenotypes are combined with label-free GMR sensor technology that allows for highly reliable screening tests. In an embodiment, the sensor system uses a novel compact construction so that it can be portable.

Figure 1:
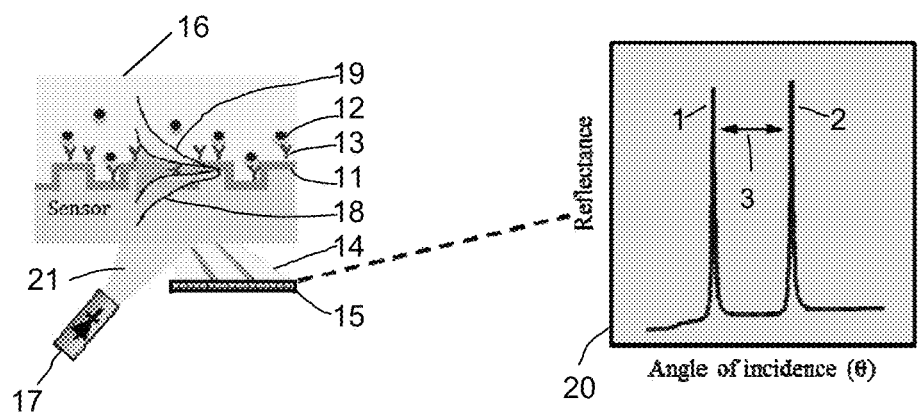
FIG. 1. Schematic of a label-free guided-mode resonance sensor system operating in angular reflection mode.

These compact optical systems are designed to be easy to use and have the capability to measure multiple agents simultaneously and in real time. One aspect of the invention is to identify and quantify protein biomarkers that are either up- or downregulated in blood and serum associated with disease (such as ovarian serous papillary carcinoma). Detection sensitivity is estimated in the picomolar (pM) to micromolar (µM) range to detect disease-induced alterations in protein concentration indicative of disease progression. This portable system is based upon guided-mode resonance sensor technology [16-18]. Advantages of this approach include high accuracy and capability to quantify the presence of molecules without requiring extensive chemical processing or washing steps. A strong reflected signal response 1 (or alternatively transmitted null) enables the use of low power electronics to make this a compact, end-user-targeted and portable system that is as easily applied as widely used blood glucose or blood pressure monitoring devices. Sensor selectivity is imparted using robust surface chemistries such as antibody and aptamer layers that will only react with a targeted analyte. A schematic of a label-free guided-mode resonance sensor system operating in reflection mode is shown in FIG. 1. The diverging 21 (expanding) beam from the laser diode (LD) 17 is incident on the sensor element with a continuous range of angles. As binding events occur at the sensor surface 11, resonance peak changes can be tracked as a function of incident angle ($\Delta\theta$) 20. The resonance occurs at different angles for TE (transverse-electric light: laser-light electric field vector normal to the plane of incidence) and TM (transverse-magnetic light: magnetic field vector normal to the plane of incidence) polarization states of the input light enabling high-accuracy, cross-referenced detection. The incident light excites photonic surface states shown as TE 18 and TM 19 modes. As schematically indicated, these modes interact differently with the surrounding media enabling the polarization-based differentiation. As the sensor surface 11 is exposed to the sample under test 16 and a chemical binding event occurs between the selective agent (such as an antibody layer 13) and the analyte to be detected 12 (contained in the sample 16), the reflected resonance response(s) 14 are monitored and tracked in real-time on a detector array 15. No post-processing is typically required. In this approach, the relative angular shift 3 between the baseline 1 (before the reaction starts) and the end of the reaction 2 can be used to qualify the presence of the analyte 12 in the sample 16 and/or quantify the concentration.

In one embodiment, this invention is a multi-channel portable biochemical detection system for screening biomarker proteins in blood and serum as indicators of ovarian serous papillary carcinoma. The system can be used to determine a temporally distinct diagnosis for monitoring presymptomatic aspects of the disease, disease progression and the efficacy of intervention therapies. The invention can also be used to distinguish quantitatively between primary and metastatic ovarian serous papillary carcinoma through differential protein quantification. Such information may be valuable for therapeutic decision-making and the development of differential diagnostic and therapeutic strategies. FIG. 1 shows a schematic of the basic sensor employing simultaneous dual readout of the same reaction by engaging both available polarization states.

In another aspect of the invention, the portable diagnostic tool can be employed as routine clinical diagnostic tool by persons with minimal training and technical expertise. For instance, a home-monitoring device for patients suffering from chronic disease conditions that require monitoring of disease progression and evaluation of the success of intervention therapies is envisioned. This system can be extended to a wide variety of portable sensing applications, including telemedicine. The basic sensor platform can be extended to a high-density chip that can test for thousands of biomarkers and/or DNA/RNA in a single patient sample.

Guided-Mode Resonance Approach

Portable monitoring devices that are simple and accurate are critically needed to improve medical services and to reduce cost. Practical clinical and home use of these monitoring devices requires a system that can utilize low-power mobile electronics and standard interfaces, such as USB or wireless transmission. Sensor systems that can be integrated into miniature, self-contained battery- or solar-powered footprints may also be desirable.

Conventional biosensor technologies are limited by some or all of the following weaknesses:
1. Low signal integrity requiring bulky and power hungry electronics to operate.
2. Complex operation due to time-intensive chemical processing steps.
3. Real-time results not available.
4. False readings due to sample density variations, temperature fluctuations, and non-targeted interferences such as dust or contaminants.
5. Limited architectures for mobile implementations.
6. Surface chemistries degrading over time.

Ideally, what is needed is a biosensor technology that provides:
1. Accurate, portable sensor system that is simple to operate.
2. No chemical processing or long incubation steps.
3. High signal-to-noise (S/N) ratios that enable low-power electronics with standard interfaces.
4. Cross-referenced data that reduces false readings.
5. Real-time results.
6. Capability to perform a wide range of biomolecular assays.

The present inventors have determined that biosensors employing the guided-mode resonance (GMR) effect that occurs in subwavelength waveguide gratings provide accurate biosensors and, in particular, provide suprising beneficial results in detection of biomarkers indicative of disease states. When these sensors are illuminated with a light source, a specific wavelength of light is reflected (with a corresponding transmission null) at a particular angle. Interaction of a target analyte with a biochemical layer on the sensor surface yields measurable angular shifts that directly identify the binding event without additional processing or foreign tags. Since the resonance layer is polarization sensitive, separate resonance peaks occur for incident TE and TM polarization states. Moreover, very conveniently, the layer can be designed to support additional resonant leaky modes, thereby providing additional resonance peaks for further increased detection accuracy and reduction of the probability of false readings. This property provides cross-referenced data points that can be used to calibrate for variations such as temperature or sample background density. The sensor is multifunctional, as only the sensitizing surface layer needs to be chemically altered to detect different species. The sensor element can be prepared with standard surface chemistries to covalently attach a selective layer (for example, antibodies or aptamers). Commercially available blocking agents are used to minimize non-specific binding effects in non-ideal backgrounds such as serum and cell culture supernatants. As the binding assay begins, the analyte binds to the detection layer target, and a change in the resonance response is tracked on an imaging detector array (such as a CCD or CMOS camera). The amount of the resonance peak shift can be directly correlated to the quantity of analyte in the fluid. Operation in both air and water environment is possible. Sensors responsive to changes varying from the nanoscale (<0.1 angstroms) up to several microns are possible. Thus, the same basic sensor technology can be used to detect binding events at the molecular level as well as to monitor attachment of larger bacterial analytes (~2 µm). Commercial fabrication processes can be used to produce the resonant grating sensor element in low-cost polymer materials by molding.

Compelling attributes of this new sensor technology include:
1. Label-free operation minimizes chemical processing.
2. Highly sensitive operation for a wide range of biosensor applications.
3. Multiple resonance peaks with polarization diversity provide cross referenced data such that:
   a. False readings are minimized;
   b. Background variations can be distinguished from targeted reactions.
4. Sharp, well-defined resonance reflection peaks provide accurate, high-resolution data.
5. High signal-to-noise ratio enables the use of low power light sources and detectors.
6. Capability for ultra-compact, highly integrated sensor element and system.
7. Dense biochip format is available for parallel multi-species detection with sensor arrays.

Figure 2:
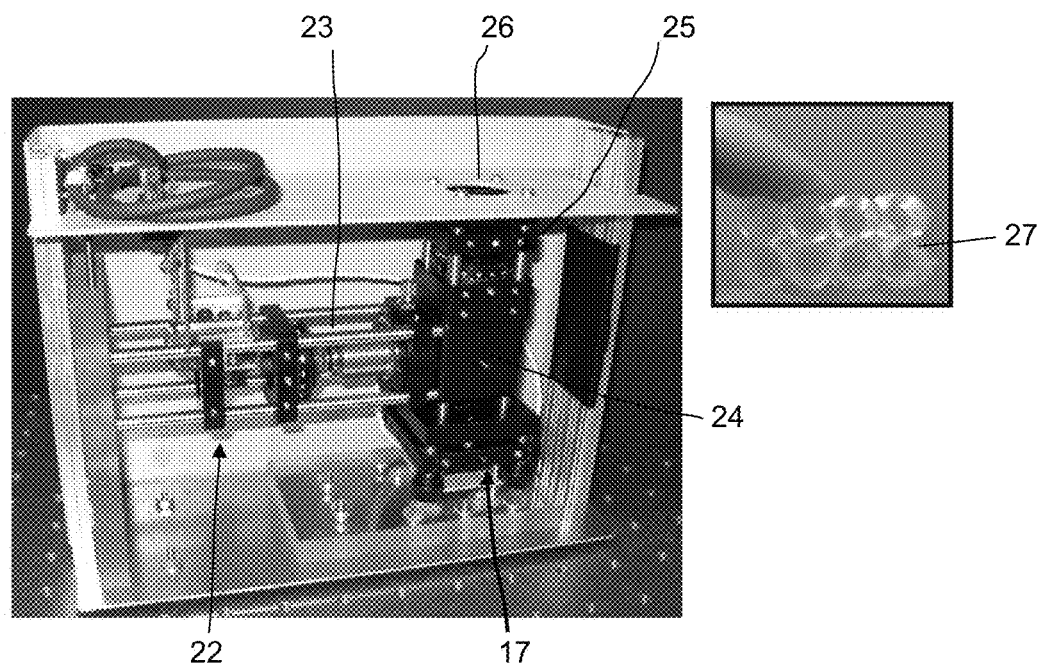
FIG. 2. Illustration of a single channel GMR sensor system.

In an embodiment of the invention, we provide a compact sensor system that can integrate commercially available low-power mobile electronics with a new highly sensitive sensor technology that greatly simplifies medical diagnostic tests. Simplified assay processing can significantly reduce operation complexity compared to standard tests such as enzyme-linked immunoassays. Sensor elements can be made in low-cost polymers (or glasses) and can be pre-sensitized to detect an array of agents. These elements can be disposable and designed to operate with a liquid sample. Additionally, the sensor system design can utilize low-power laser diodes and detector arrays in a compact format. This can provide a truly portable platform that is simple to operate and requires minimal power. FIG. 2 shows an example single-channel sensor system. In this embodiment, laser light 17 is passed through a beam shaping lens 25 to focus the incident light on the sensor element 27 mounted on the reader 26. The reflected signal from the sensor element 27 is then redirected by the beamsplitter 24 to a CMOS detector array 22 for readout. A lens 23 can be used in front of the detector array 22 to optimize the detected signal. Power can be provided by USB port interface or small on-board battery (not shown).

Moreover, we describe experimentally demonstrated system prototypes utilizing the GMR angular-based detection in a reflection format. We compare absolute and relative protein levels of biomarkers for ovarian cancer in relevant cell lines of various disease stages utilizing traditional quantitative Western blot analysis and the GMR detection approach. The biomarker proteins chosen in this invention were based on published genomic and proteomic data that suggested their up-regulation either in primary ovarian carcinoma or in late-stage advanced metastatic carcinoma. In order to provide relevant samples for analysis, five cell cultures of established in vitro model systems for ovarian cancer were chosen that represented various stages of ovarian cancer. Culture supernatants were collected after confluency to provide samples containing expressed biomarker proteins. Our data shows the differential release of the selected proteins in the various ovarian cancer cell lines, confirming their potential to serve as biomarkers for distinguishing primary versus metastatic ovarian cancer. Importantly, quantification of biomarker proteins was consistent between Western blot and the GMR detection system. We conclude that our novel detection system is suitable for quantification and detection of novel biomarkers of primary and metastatic ovarian cancer.

Guided-Mode Resonance Sensor Technology—Discussion of Key Figures

Thin-film structures containing waveguide layers and periodic elements (photonic crystals), under the correct conditions, exhibit the guided-mode resonance (GMR) effect [1,19-32]. When an incident wave is phase-matched, by the periodic element, to a leaky waveguide mode, it is reradiated in the specular-reflection direction as it propagates along the waveguide and constructively interferes with the directly reflected wave. Conversely and equivalently, the phase of the reradiated leaky mode in the forward, directly-transmitted, wave direction is $\pi$ radians out of phase with the direct unguided transmitted wave, thereby extinguishing the transmitted light [24]. This picture of the resonance effect pertains to a reflection, or bandstop, filter. We have additionally shown that GMR operation in transmission mode, or as a bandpass filter, is possible.

Figure 3:
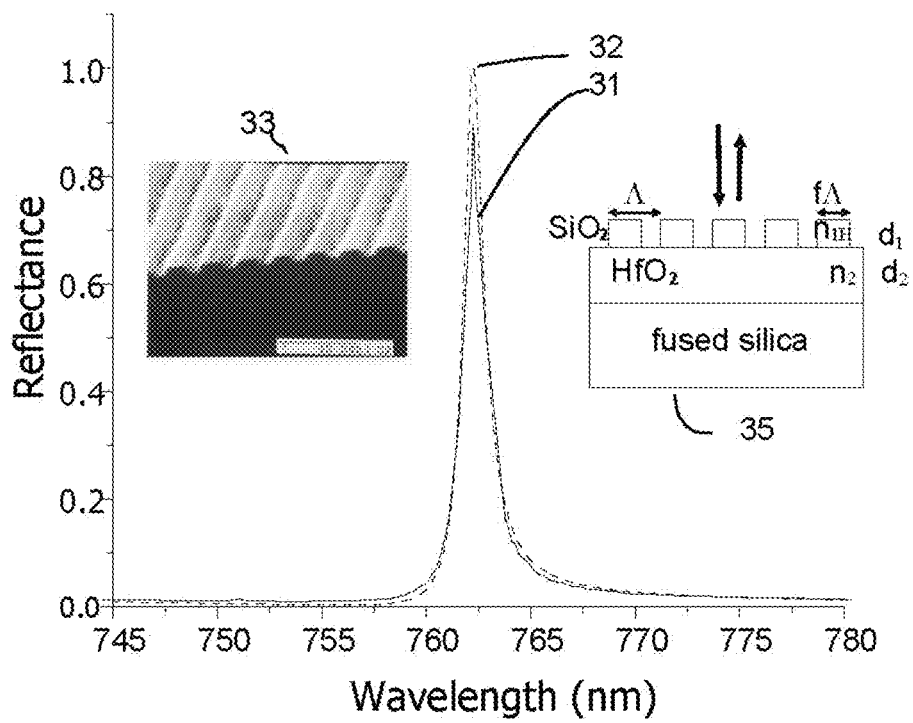
FIG. 3. Comparison between experiment and theory for a dielectric resonance element.
Figure 15:
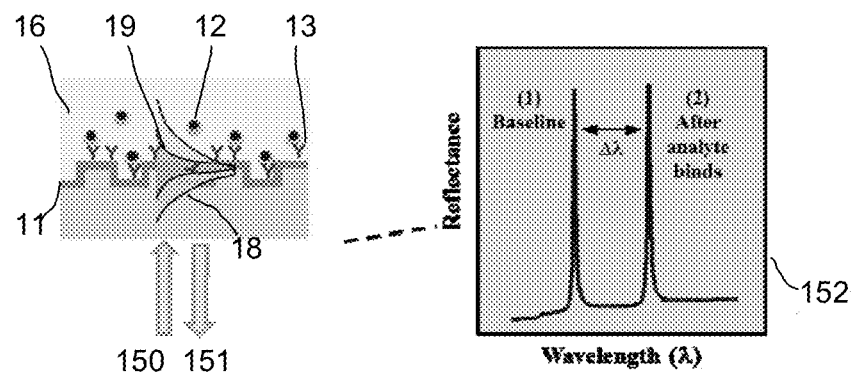
FIG. 15. (a) Spectroscopic detection system utilizing GMR biosensor technology. (b) Image of the fully automated detection system. This bioassay reader utilizes microwell array plates incorporated with a GMR sensor (shown in FIG. 13b).
Figure 15:
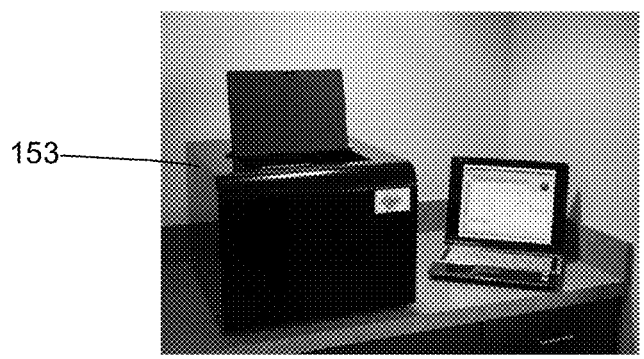

These resonant structures, tunable on change of refractive index and/or thickness, have applications for biosensors. The buildup of the attaching biolayer can be monitored in real time, without use of chemical tags, by following the corresponding resonance shift [1-4]. A new class of highly sensitive bio- and chemical sensors has thus been enabled. This sensor technology is broadly applicable to medical diagnostics, drug development, industrial process control, genomics, and environmental monitoring. Due to the features of this technology, several sensor reader system architectures are possible. For example, the GMR response during a biochemical detection event can be monitored by detecting angular resonances (FIG. 1) or spectral resonances (FIGS. 3 and 15). In one embodiment of the invention, we propose to implement an angular architecture to enable compact layouts desirable for portable systems. The spectral approach requires a bulky and costly optical spectrum analyzer. Both approaches are highly sensitive with consistently detectable shifts to achieve sensitivities in the lower pM range for antibody-antigen and aptamer-biomarker interactions. By monitoring the resonance in angle, very compact, low power and cost effective systems can be realized.

Experimental Bandstop Filters:

FIG. 3 shows the measured 31 and calculated 32 spectral reflectance of a dielectric guided-mode resonance device. The parameters used for the theoretical curve fit are close to the nominal values; they are $n_c=1.0$, $n_1=1.454$ ($SiO_2$), $n_2=1.975$ ($HfO_2$), $n_s=1.454$, $d_1=135$ nm, $f=0.58$, $d_2=208$ nm, $\lambda=446$ nm, $\theta=0°$. Rigorous coupled-wave analysis (RCWA) is used for the computations [33]. A scanning electron micrograph (SEM) 33 and a schematic of the device 35 are also shown. This device acts as a bandstop filter with the spectrum of interest reflected in a narrow band with relatively low sidebands. Although the theoretical calculation predicts 100% peak efficiency for a plane wave incidence, it is diminished in practice by various factors such as material and scattering losses, incident beam divergence, and the lateral device size; here the experimental peak is 90%. The fabrication of this device is detailed in [34].

Figure 4:
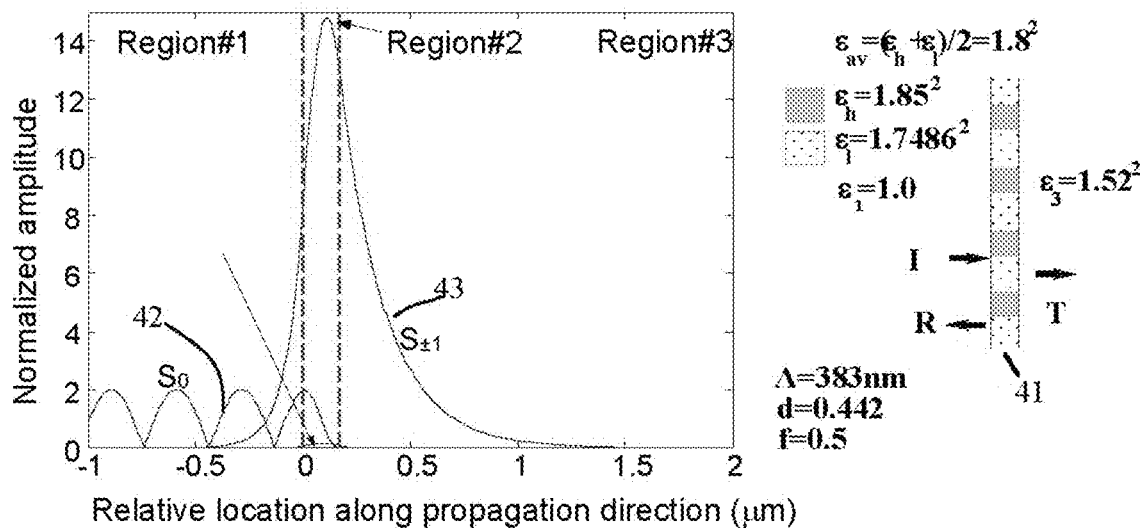
FIG. 4. Profile of the leaky mode at resonance. The amplitude is normalized to the incident wave amplitude. The results are obtained with rigorous coupled wave analysis RCWA calculations. Region 2 contains the resonant layer.
Figure 5:
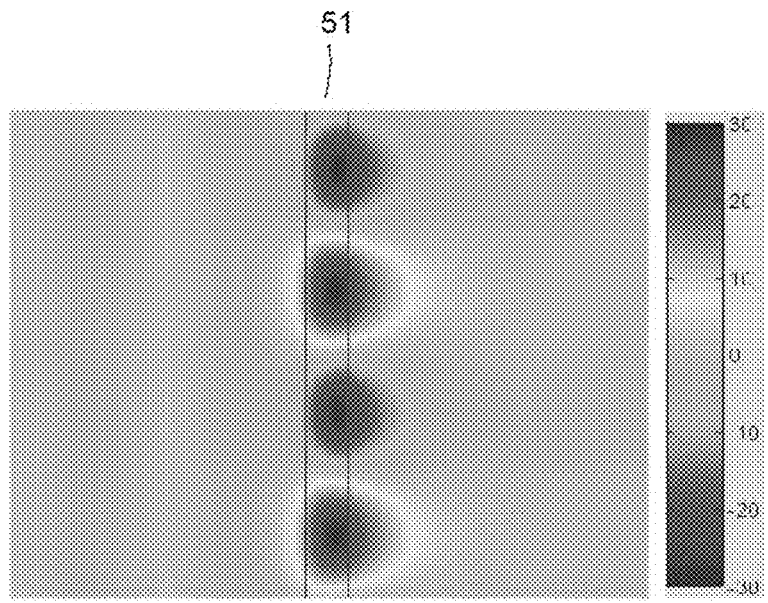
FIG. 5. Snapshot of the standing-wave pattern associated with the leaky mode in FIG. 4. The size of region is $2\lambda \times 2\Lambda$.

Leaky-Mode Field Structure and Sensor Operation:

In addition to the reflection/transmission properties of propagating electromagnetic waves, the near-field properties of resonant periodic lattices, including localization and field-strength enhancement, are of interest in sensor applications. The near field patterns associated with a simple example structure are presented here by considering a single periodically modulated layer 41 (inset in FIG. 4) surrounded by regions of lower average refractive index (or dielectric constant $\in=n^2$) with a normally incident TE-polarized wave. Numerical results are obtained with rigorous coupled-wave analysis (RCWA) [33] to provide quantitative information on relative field strengths and spatial extents associated with the near fields. As shown in FIG. 4, the $S_0$ wave 42 ($S_0$ denotes the electric field of the zero diffraction order) propagates with reflected wave amplitude close to unity producing the standing-wave pattern shown by interference with the unit-amplitude input wave. Thus, at resonance, most of the energy is reflected back. The evanescent, first-order diffracted waves $S_1$ and $S_{-1}$ 43 constitute the counter-propagating leaky modes; these are excited by the incident light. Because the grating layer is used as both waveguide and phase matching element in this case, the maximum field value is located in the grating layer with the evanescent tails gradually penetrating into the substrate and cover. FIG. 5 shows the standing wave pattern 51 formed by the counter-propagating $S_{-1}$ and $S_{+1}$ waves 43 at a certain instant of time. Since the $S_{\pm 1}$ space harmonics 43 correspond to localized waves, they can be very strong at resonance; here the field enhancement is ~×14 as seen in FIG. 4. Depending on the level of grating modulation ($\Delta\epsilon = nH^2 - nL^2$), the field amplitude can range from ~×10-×1000 in the layer relative to the input wave amplitude which represents a large increase in local intensity I~S2. The maximum amplitude of S1 is approximately inversely proportional to modulation strength. In general, small modulation implies narrow linewidth $\Delta\lambda$ and a large resonator Q factor $Q=\lambda/\Delta\lambda$.

The structure of the local fields associated with the resonant leaky modes is important to sensor applications. The leaky mode is a surface state that propagates along the surface providing maximal interaction with any attached molecular or chemical layers. In the technology invented herein, the sensing field (a resonant leaky mode) is maximized in the grating layer with an evanescent tail penetrating into the cover region (clearly shown in FIGS. 4 and 5).]

Polarization Diversity:

Polarization is a fundamental property of light. As a beam of light can possess arbitrary polarization states, the incident beam polarization state can be engineered cost-effectively to improve sensor performance provided that the sensor is physically capable of responding to such states. The GMR sensor in accordance with an embodiment of the present invention has this capability since the resonance response is sensitive to the incident light polarization. Thus separate resonance peaks occur for incident TE and TM polarization states. This property provides enriched data sets useful for increasing detection accuracy in a given sensor element. The incident light excites photonic surface states shown as TE and TM modes. As schematically indicated in FIG. 1, these modes interact differently with the surrounding media, enabling the polarization-based differentiation. The important point is that separate reference channels are not required to distinguish, for example, thermal background variations during data acquisition. This improves accuracy and reduces cost. Sensors arrays based on other concepts may apply a significant fraction of their sensor elements as reference monitors, which is not an efficient use of the chip.

Figure 6:
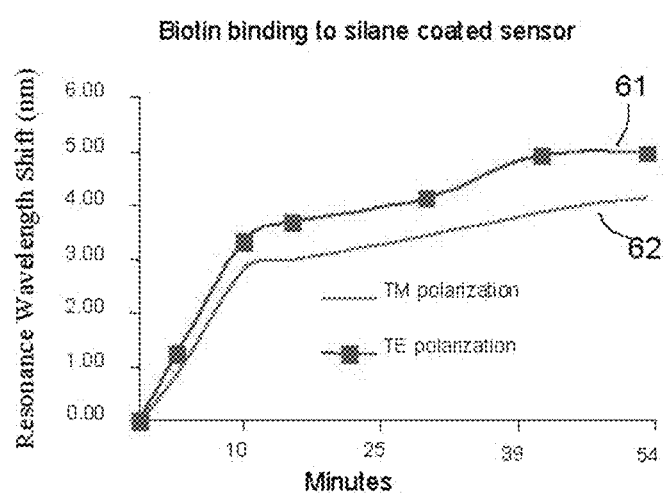
FIG. 6. Illustration of data collected when using GMR sensor with polarization diversity to quantify biotin binding (0.5 mg/ml Sulfo-NHS-LC-Biotin) to a silane-coated sensor surface. The molecular attachment event is monitored as function of time. Results for both TE and TM polarizations are shown. The results are consistent and exhibit the differing sensitivities associated with differing polarizations. At the end of the binding, any loose or unbound biotin is rinsed away in PBS-Tween solution.
Figure 7:
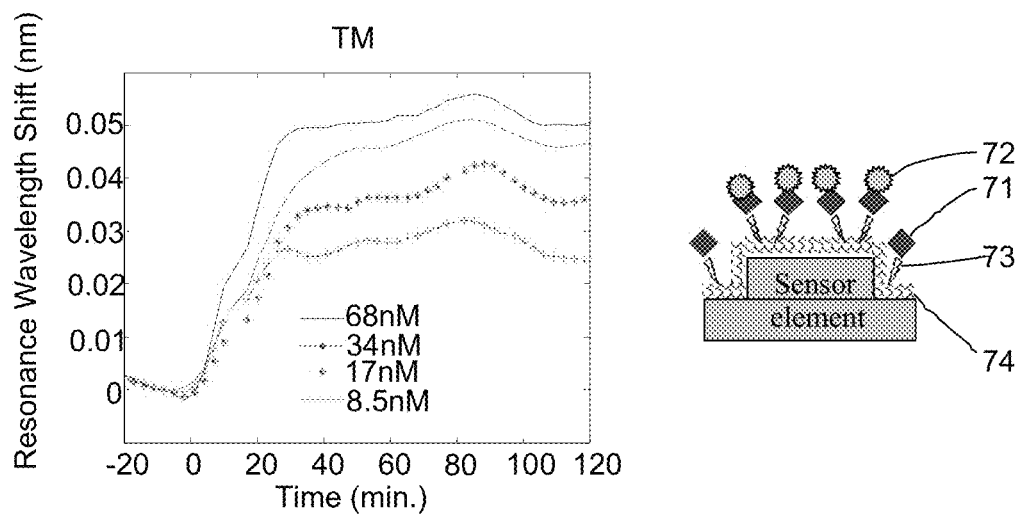
FIG. 7. Resonance peak wavelength shift as a function of time for calreticulin binding to its matched IgG antibody. Solutions are monitored with calreticulin concentration range of 8.5 nM to 68 nM. A PBS blank is used as a reference and subtracted from the data. At t=0, the calreticulin solutions are introduced to the sensor element and monitored in real time for 80 minutes. At t=80 minutes, the calreticulin solution is removed and the sensor element is washed thoroughly with PBS/Tween and monitored for another 40 minutes to establish a post-binding baseline. Results are repeated in triplicate and averaged.

Using dual polarization data collection, FIG. 6 illustrates how the binding of the foundational attachment chemistries (such as silane, antibodies and biotin-avidin layers) can also be monitored in real time. When implemented in a flow-cell geometry, this approach can be used to monitor the full cycle of molecular binding dynamics to determine association and disassociation rates for applications such as proteomics. Since the present work is targeted at concentration analysis, we implement the GMR sensor in a static micro-well format 27. Monitoring of the association dynamics (such as shown in FIGS. 6 and 7) is used to determine when the reaction has stabilized to an approximate equilibrium. By monitoring the quality and uniformity of the functionalization chemistries in an assay, repeatability and accuracy from well to well can increase. In this example, a N-Hydroxysulfosuccinimide ester of biotin is deposited on a silane-coated sensor element. We use a biotin with a long chain spacer arm attached (Sulfo-NHS-LC-Biotin) that reacts efficiently with primary amines (such as silane groups) on the sensor surface. This Sulfo-NHS-LC-Biotin analyte has a molecular weight of 557 Da. Note that there are inherently separate peaks for each polarization (TE 61 and TM 62) that shift in response to the reaction. This distinguishing feature provides two concurrent sets of data that can be used to distinguish background index/density changes from the targeted antigen binding interactions, thus increasing detection accuracy and reducing false positive readings [17]. In this experiment, the TE resonance occurs near ~780 nm and the TM resonance occurs near ~795 nm.

Figure 8:
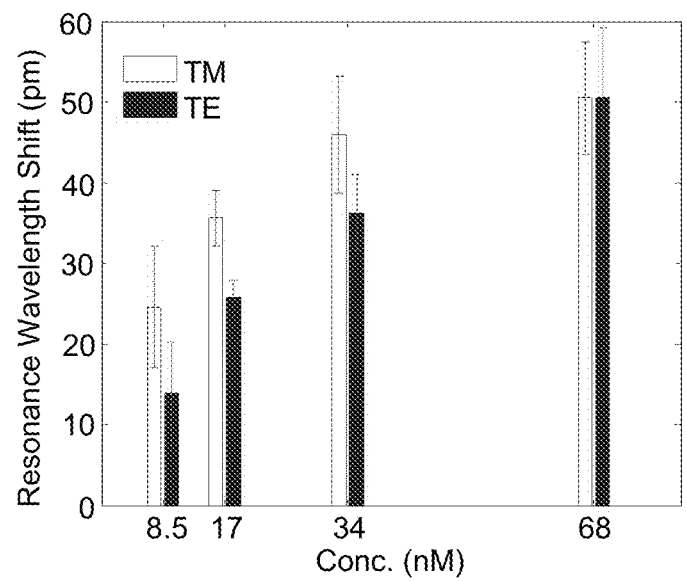
FIG. 8. Dual polarization resonance response for calreticulin binding to the activated sensor element. These results are gathered after a post-PBS/Tween wash, indicating bound calreticulin remaining on the sensor surface. A PBS blank is used as a reference and subtracted from the data. Results are repeated in duplicate and averaged. Error bars shown indicate estimated uncertainty in each measurement.

We have conducted dual-polarization experiments investigating the detection of calreticulin 72, which has a molecular weight of ~46 kDa and has an elliptical shape ~30 nm long and ~2.4 nm wide [35]. For detection of the biomarker protein calreticulin 72, the capture antibody used is a specific monoclonal IgG antibody 71 (anti-calreticulin). The sensor plates are initially coated with a commercially available silane 74 (3-Aminopropyltriethoxysilane) that provides means to covalently bond the calreticulin antibody to the sensor surface. It is chemically attached to the silane sensor surface 74 using the homobifunctional cross-linking agent 73 disuccinimidyl suberate (DSS). The sensor element is then blocked with a 3% milk solution to minimize non-specific binding. Next, the plate is aspirated and washed with PBS/Tween in preparation for use. A known standard concentration of 68 nM (3.75 μg/ml) calreticulin is used as the high standard. Buffer is used as a reference blank. A kinetic response of calreticulin binding to the antibody-coated sensor element 75 is shown in FIG. 7. The sensors are incubated in calreticulin solution for 80 minutes and subsequently washed with PBS/Tween to remove unbound material. TE and TM resonance wavelength shifts are then recorded as shown in FIG. 8. While the sensor operates in real time, the speed of detection is often limited by the biochemical binding dynamics, which can be affected by temperature, humidity and selective layer affinity.

Additionally, we have verified experimentally that this sensor approach can be applied to raw blood and serum samples with minimal sensitivity degradation. We have detected pM concentrations of interleukin-1 beta in raw blood and serum. Other selective agents that may be used include aptamers, peptides, DNA and others.

Sensor System Design Examples

In this invention, several multi-channel sensor systems are described to analyze multiple analytes using angular system architectures (FIGS. 9-12).

System Design Example 1

Figure 9:
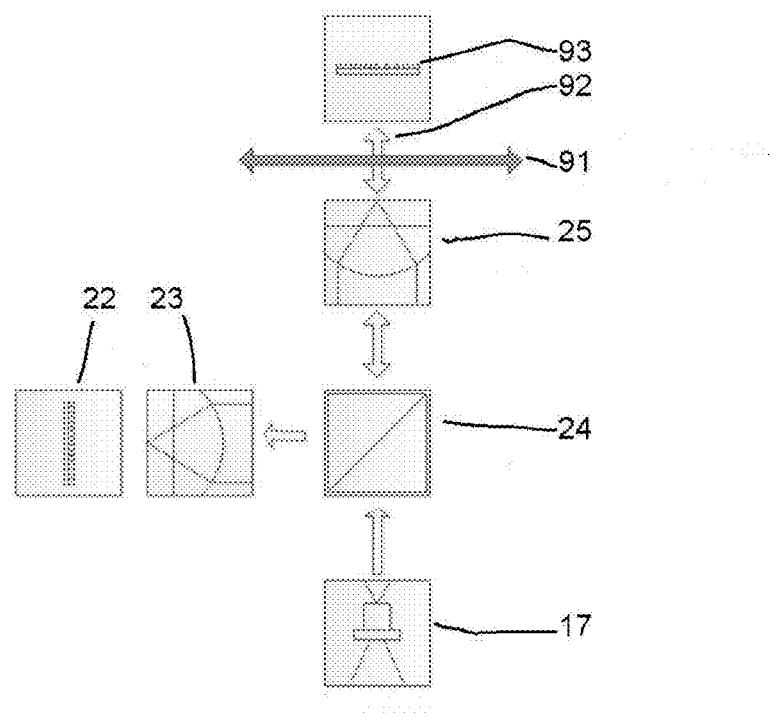
FIG. 9. Schematic of a GMR sensor arrayed system based on the fundamental design in FIG. 1.

In the example embodiment shown in FIG. 9, a focused beam from a low-power laser diode 17 (850 nm wavelength for example) is incident on the sensor element from the substrate side 92. A lens 25 is used to focus the light onto the sensor array 93. The reflected signal from the sensor element is then directed through a beamsplitting element 24 onto a high-density CMOS detector array 22 (such as those commercially available from Toshiba or others). This layout is also scalable to high-density arrays since the entire detector assembly can be scanned 91 across the bottom of an array plate 93 using an integrated translation stage. Data can be acquired via USB (or other electronic means) and down-loaded into a data file (such as ASCII text for manual processing by the user). Low power laser diodes and photodetector elements can be used due to the high signal response reflected from the sensor element. Commercially available electronics can be interfaced with the near-IR laser source ($\lambda$=850 nm) and CCD (or CMOS) detector array and tested as part of the sensor prototype system. Target angular resolutions for sensor reflected peak detection are better than 0.05 degrees corresponding to pM level detection.

System Design Example 2

Figure 10:
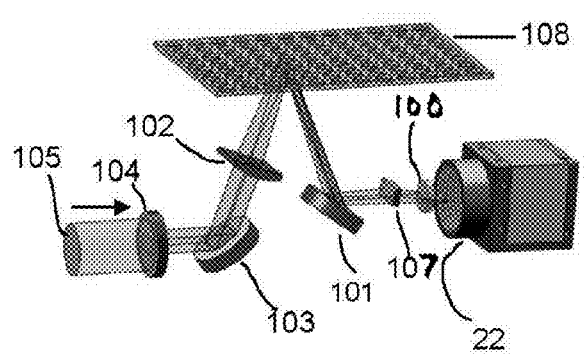
FIG. 10. (a) Schematic of the angular-based GMR system claimed in this invention. (b) The optical system described in (a) is scanned across the bottom of a GMR sensor array plate with the aid of an XY translation stage.
Figure 10:
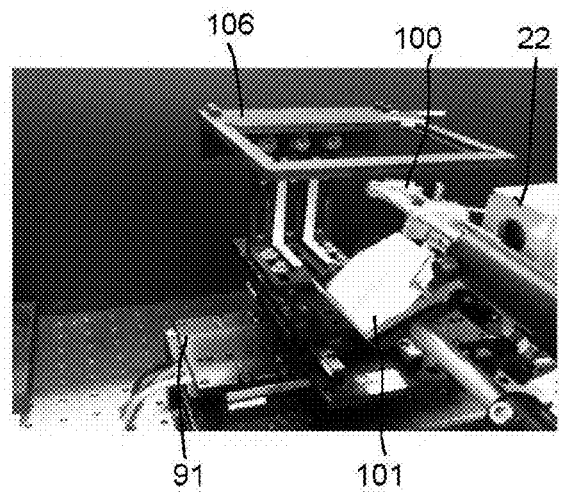

FIG. 10 illustrates a designed and assembled GMR angular system prototype. FIG. 10(a) depicts the optical path, which is scanned across the bottom of a GMR sensor array plate 108 with the aid of an XY translation stage 91 (shown in FIG. 10(b)). In this system, the input laser source 105 is collimated and directed via a mirror 103 to a plano-cylindrical lens 102. The line-focusing element 102 provides a means to interrogate the resonance sensor device with a range of incident angles using a single-wavelength source. The mirror(s) provide a means to conveniently reduce the system size by folding the incident/reflected beams. The excited resonant light is reflected from the GMR sensor element array at a specific angle and directed to a 2D CCD device 22 (Sony, 782×582 pixels) via a mirror 101. A polarizer 107 and a lens 100 are used in front of the CCD camera 22 to increase the signal-to-noise ratio of the detected resonance and provide a means to optimize the resonance linewidth and dynamic range. By adjusting the resonance line (or peak) beam divergence on the camera to cover more pixels, detection sensitivity can be increased; however, there is a tradeoff in dynamic range. As a biochemical reaction proceeds at the sensor surface, the reflected resonant line (or peak) occurs at a different angle and moves across the CCD camera pixels. It was convenient to use bottomless 96-well microarray plates that are bonded to GMR sensor elements 108 as shown in FIG. 13(b). The size of each individual microwell is approximately 6 mm, with the entire plate dimensions approximately 128 mm×86 mm. The incident beam from the line-focused laser light is ~200 microns wide and approximately 8 mm long (this covers the length of the well, but it does not read into the adjacent well). This format enables an arrayed detection in each well such that each measurement is performed in quadruplicate (or ~8×, see FIG. 11(b)). The GMR sensor elements can be constructed using polymer-molding and thin-film deposition (an AFM image 131 is shown in FIG. 13(a)).

System Design Example 3

Figure 11:
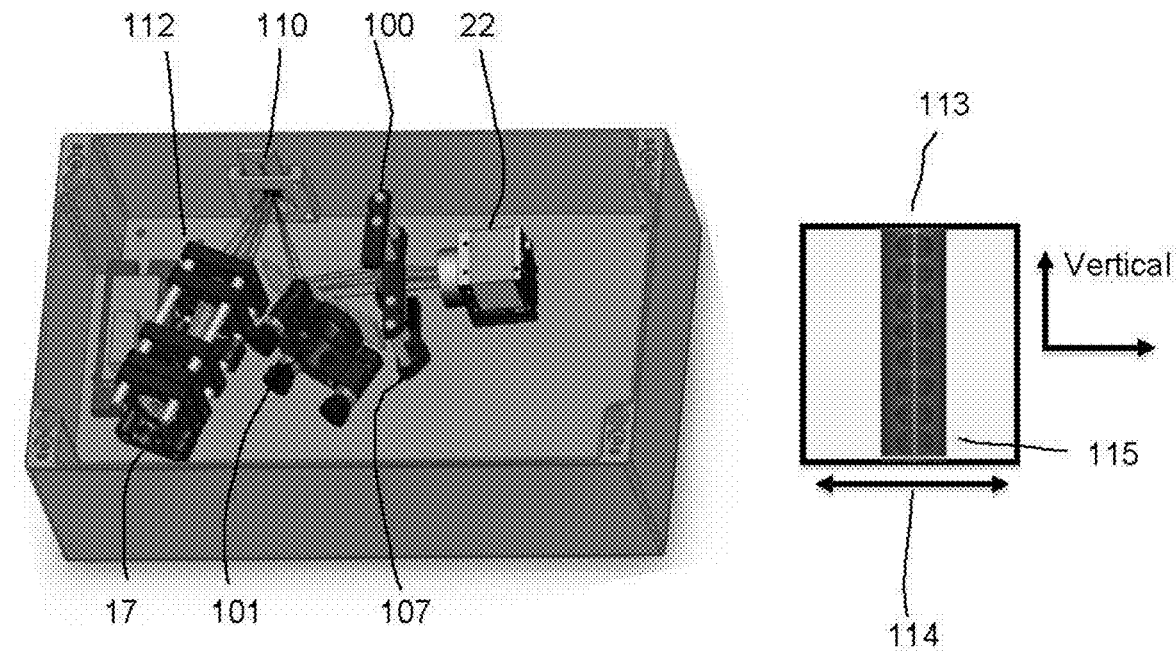
FIG. 11. (a) CAD layout of a portable system disclosed in this invention. The system is mounted in a box with a slotted lid that allows the user to insert the sensor chip for readout. (b) Optical interrogation scheme to provide a simultaneous readout of an eight-sensor element array.
Figure 12:
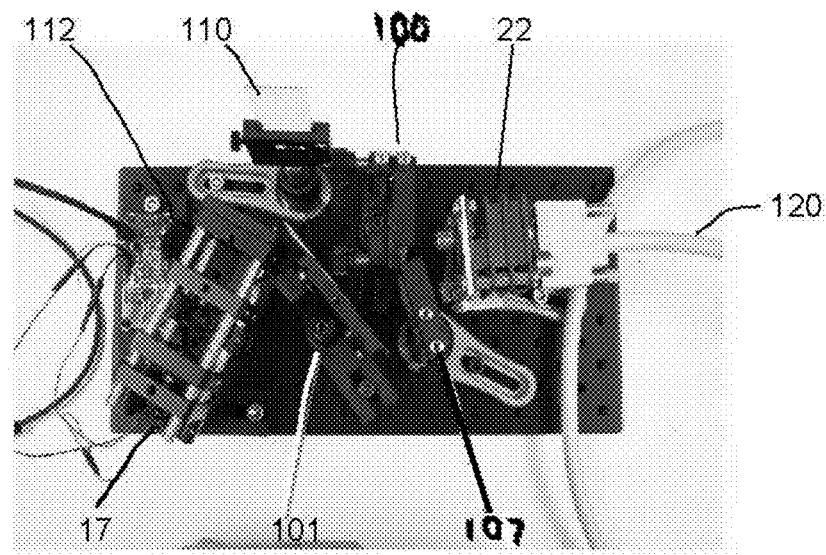
FIG. 12. Picture of the eight-channel sensor system using off-the-shelf components, and based on the design layout in FIG. 11. This assembly can be integrated in a housing to enable system portability.
Figure 37:
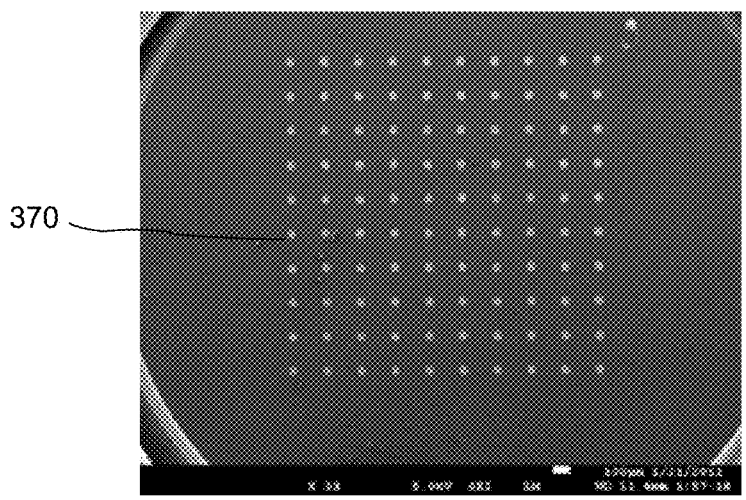
FIG. 37. A scanning electron microscope image of a 10×10 spotted silver ink array fabricated on a GMR sensor element using a microplottin machine (Sonoplot). Each spot is approximately 50 microns in diameter with 100-micron spacing.

This invention discloses a portable detection system. In one embodiment, we designed and built a smaller integrated format that does not require a translation stage and can simultaneously read an array of sensor elements (FIG. 11). This format can readily be expanded for the capability to measure 100's or 1000's of multiple agents simultaneously and in real time without moving parts. FIG. 12 shows an assembled compact system prototype based on the design described in FIG. 11. By shaping the input laser diode 17 light with a line-focusing element 112 and imaging the reflected resonance response on a detector array (such as CCD or CMOS camera 22), an eight-element (or more) GMR sensor array 110 can be read simultaneously (FIG. 11(b)). A mirror 101 may be used to fold the optical path in order to reduce the overall system size. Expansion of this concept can be envisioned to include an array of plano-cylindrical lenses that provide a simultaneous interrogation of up to 100 channels (or more). The size of the prototype shown in FIG. 12 is approximately 320 (L)×190 (W)×122 (H) mm. The GMR sensor device 110 is shown (in FIG. 13(c)) integrated on a microscope slide holder. The GMR sensor element is designed such that a spotted array of antibodies 370 (spots of ~50 to 100 microns in diameter as shown in FIG. 37) can be used to define the sensor regions in this biochip format. The system size can be greatly reduced utilizing customized components to build a miniaturized system. This design can accommodate a full array of at least eight biomarker analytes (including positive and negative controls). The submicron periodic grating profile may be seen in FIG. 13(a) from the atomic force microscope picture 131.

Figure 14:
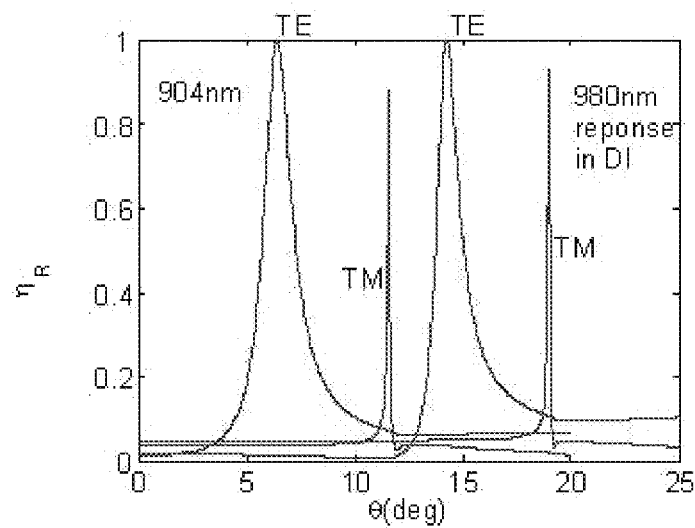
FIG. 14. (a) Computed results using rigorous codes to predict the GMR resonance locations for two different incident wavelengths (904-nm peaks on the left, and 980-nm peaks on the right) for operation in deionized water (DI). Optimized detection sensitivity using both TE and TM resonances during detection is attainable. (b) Snapshot of the GMR element response on a CCD camera using the 904-nm laser source. The narrower line on the left side is the TM-polarization resonance (~horizontal pixel 100), and the broader line on the right side is the TE resonance (~horizontal pixel 350). The resonance lines will move across the CCD camera as the reaction proceeds.
Figure 14:
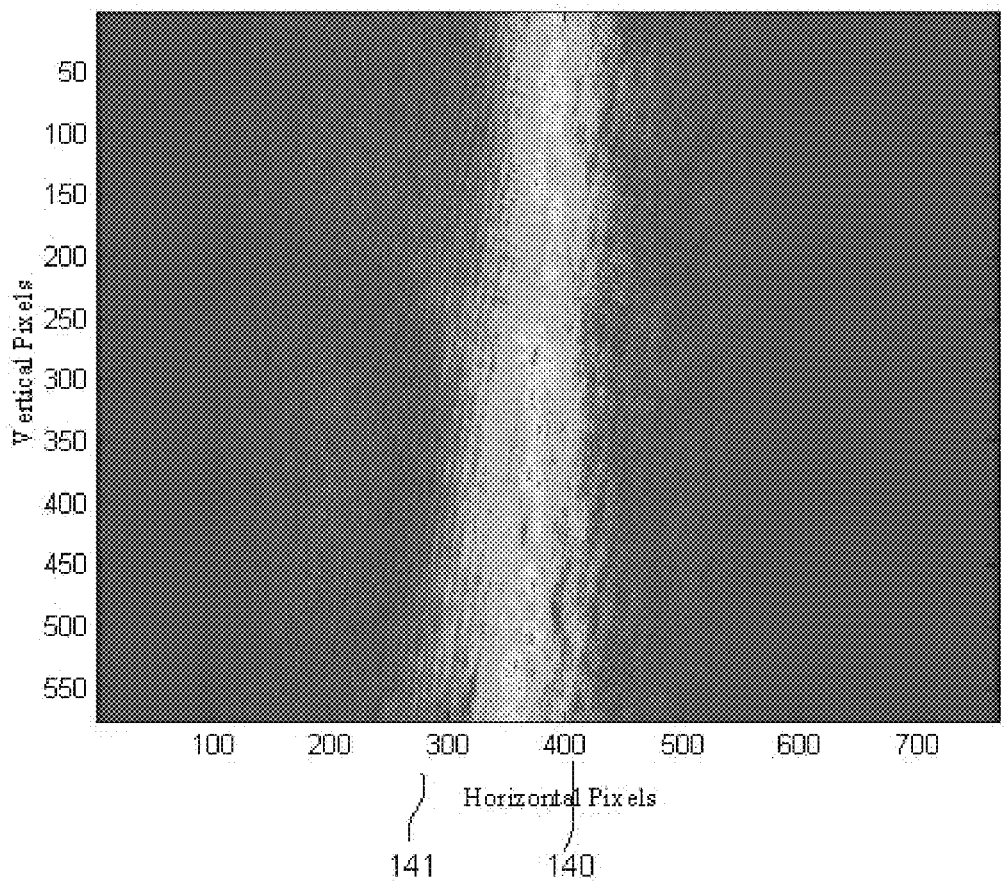

The detected signal from the CCD detector may be received via USB to a laptop PC that runs a program to control the data acquisition, signal analysis, and data statistics (completed in commercial programs such as MATLAB or others). FIG. 14(a) shows the calculated TE and TM resonance responses for two different incident wavelengths (904 nm and 970 nm) on a GMR sensor element in a water environment. The sensor is a ~500 nm period grating molded in a polycarbonate polymer and overcoated with a ~100 nm layer of $TiO_2$. FIG. 14(b) shows a CCD snapshot of the GMR sensor response operating in reflection in DI water. The resonance response is sensitive to the incident light polarization. The sensor spectral response is predicted using our existing computer codes based on rigorous coupled-wave analysis (RCWA). Employing the RCWA method, we have written efficient computer codes to solve the general multilayer diffraction problem underlying resonant sensors. This strong capability allows us to rapidly optimize sensor performance and design parameters. The lines in the CCD image shown in FIG. 14(b) correspond to the measured resonance locations predicted in FIG. 14(a) for the 904 nm source. The narrower line on the left side (at ~horizontal pixel 100) is the TM-polarization resonance 141, and the broader line on the right side is TE resonance 140 (at horizontal pixel 350). The resonance lines will move across the CCD camera as the reaction proceeds. We zoom in to the region close to one of the resonance lines to achieve high detection limits and maximize operational dynamic range.

The exact resonance peak location on the CCD imager is determined by using a peak-fitting algorithm in MATLAB. Before determining the resonance peak locations, the acquired raw image is filtered using a low-pass filter algorithm (also in MATLAB). The reflected angular location is tracked as a function of time using a software program such that quantified and/or qualified results can be obtained.

Based on experiments utilizing the systems described in FIGS. 9 and 12, we have tabulated an example selection of key parameters for the prototype sensor system design (Table 1). An estimated reflected resonance peak shift as small as 0.2 pixels can be resolved with these systems (FIGS. 9-12). These specifications are based on known GMR sensor element parameters and commercially available optical lens/imaging camera performance parameters. The systems were tested and optimized using 904-nm, 980-nm, and 630-nm wavelength sources. Experiments detecting biomarkers for ovarian cancer have been performed using the reader system design shown in FIG. 11. A laser with wavelength 630 nm is used as the light source in the biomarker tests (using only TM polarization). The incident wavelength is chosen to optimize detection sensitivity and dynamic range for biomarker detection in these experiments using the current sensor element design.

TABLE 1

Example optical performance parameters for systems described in FIGS. 9-12

| Index | Parameter | Symbol | Value | Notes |
|---|---|---|---|---|
| 1 | Bulk index resolution | $R_{bulk}$ | <1e−5 RIU | Depends on sensor design |
| 2 | Operating wavelength | $\lambda_{res}$ | 904 nm | Chosen (optimized for portable layout here) |
| 4 | Bulk index sensitivity | $S_{bulk}$ | 15 deg RIU$^{-1}$ | $S_{bulk} = \Delta\theta/\Delta n_{bulk}$ |
| 5 | CCD imaging sensor pixel pitch | $\Lambda_{CCD}$ | 8.3 um | Sony ICX415AL |
| 6 | CCD number of horizontal pixels | #Pixel$_H$ | 782 | Chosen with CCD |
| 7 | CCD number of vertical pixels | #Pixel$_v$ | 582 | Chosen with CCD |
| 8 | Total number of channels along horizontal direction | #Chan | 8 | Chosen based on required channel density |
| 9 | Pixels available to each horizontal channel | #Pixel$_{HC}$ | 260 | #Pixel$_{HC}$ = #Pixel$_H$/#Chan |
| 10 | Angular resolution | $R_{angular}$ | 1.5e−4 degree | $R_{angular} = R_{bulk} * S_{bulk}$ |
| 11 | Dynamic range - angular | $DR_a$ | 0.78 degree | $DR_a$ = #Pixel$_{HC}$/PL$_{ratio}$ |
| 12 | Dynamic range - bulk index | $DR_b$ | 0.052 RIU | $DR_b = DR_a/S_{bulk}$ |
| 13 | Central resonance angle | $\theta_{res}$ | 8 degree | Chosen based on sensor design |
| 14 | Minimum peak shift resolution | #Pix$_{res}$ | 0.18 pixels | Measured noise floor |

Spectroscopic Benchtop Reader Example

A benchtop spectroscopic system reader tracks changes in resonance peak location in wavelength 152 (as shown in FIG. 15) rather than in angle 20 as described above. Collimated light from a broadband light source 150 is incident on the sensor element and the reflected narrowband resonance response 151 is monitored in wavelength 152 as binding events occur at the surface of the sensor element 11. This approach utilizes an optical spectrum analyzer to monitor wavelength changes during a biochemical event. Similar to the angular approach described in FIG. 1, we can monitor both TE resonant mode 19 and TM resonant mode 18 responses during operation. This spectroscopic reader system is fully automated and can scan a 96-well GMR sensor array plate in less than 1 minute. A commercial grade system 153 utilizing this approach is shown in FIG. 15(b). We have performed side-by-side testing using the angular system prototype and existing spectroscopic system to validate its use for detection of the biomarker proteins, and we found the angular system to have comparable performance. However, advantages of the angular format developed in this invention include system size and cost. The spectroscopic system requires a bulky and expensive optical spectrum analyzer, while the angular system can utilize portable electronic components such as CMOS/CCD cameras that are low cost and extremely compact. Data taken with the spectroscopic system tracks wavelength changes in nanometers (Resonance Peak Shift (nm)), while the angular system results denote resonant shift pixel shifts (Resonant Peak Shift (pixel)).

GMR Sensor Element Fabrication

Figure 13:
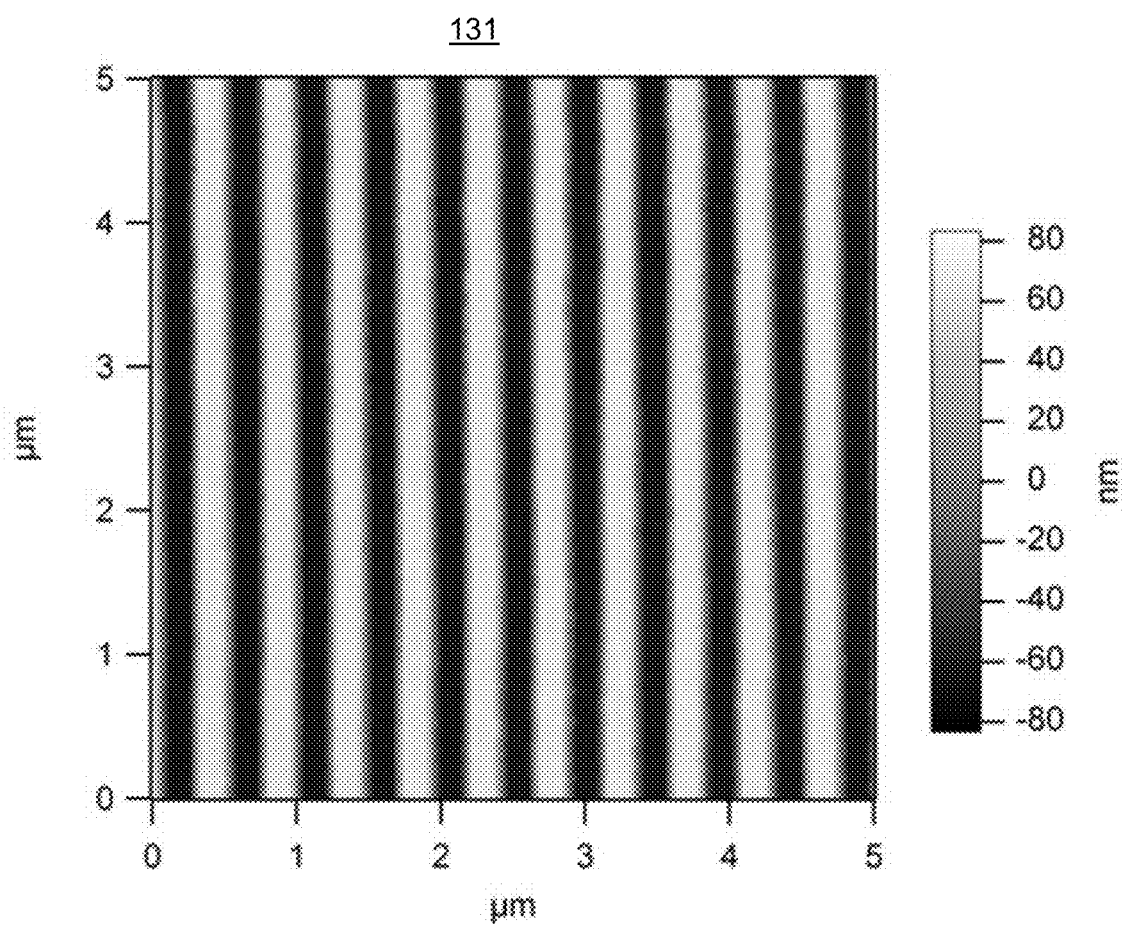
FIG. 13. Sensor devices used in this invention. (a) Atomic force microscope image of the ~500-nm period molded grating. This plastic molded element is coated with a 100-nm thick layer of $TiO_2$ or $HfO_2$ to create a guided-mode resonance device. (b) A 96-well bottomless microarray plate is integrated with a GMR device in this invention. (c) A biochip format GMR sensor shown accommodates the smaller footprint system developed in FIGS. 10-12. The microscope slide is also used as a mounting handle to insert into the system for readout. A green diffraction spectrum is visible.
Figure 13:
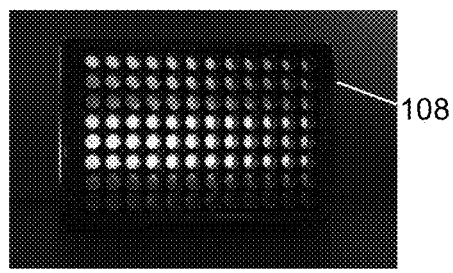
Figure 13:

We fabricate GMR filters and sensors in dielectric media such as moldable polymers, fused silica, silicon dioxide, hafnium dioxide, silicon nitride and other materials. The GMR biosensors may embody a single-layer filter design fabricated using low-cost submicron molding methods. We utilize polymers imprinted with submicron grating patterns (~500 nm grating periods) and coated with a high-index dielectric material (such as $TiO_2$ or $HfO_2$) to realize resonant sensors. FIG. 13 shows an example of a GMR sensor 131. A single sensor design was implemented in a microarray format for biomarker experiments (FIG. 13b) and a chip format for the compact reader system 110 (FIG. 13c). These sensors are designed to operate in the near-IR wavelength range (700-900 nm), where most biochemical materials have minimal absorption.

Sensor Design and Fabrication Examples

The sensor spectral response is modeled using our existing computer codes based on rigorous coupled-wave analysis (RCWA) assuming plane waves incident on structures with infinite dimensions in the plane of the grating [33]. We have developed computer codes that efficiently handle general combinations of periodic and homogeneous layered structures. We use these codes to design the sensors for specific spectral regions and diverse application scenarios. Because of the plane-wave assumptions used, these codes run extremely fast and are found to be highly reliable as verified by repeated comparisons with experimental results. For example, FIG. 3 shows the measured and calculated spectral reflectance of a dielectric GMR device. Additionally, coupled-wave electric and magnetic spatial field distributions, including resonant leaky-mode amplitudes, can be conveniently and efficiently computed with RCWA. The RCWA code can be used to extract thickness/refractive-index information from measured biochemical adhesion events by comparison with experiment. This is analogous to the extraction of thin-film thickness and complex refractive index in ellipsometry. Another useful design tool is the finite-difference time-domain (FDTD) analysis method. We use this method to model finite structures and time-varying fields.

Ovarian Cancer Biomarker Screening Approach

Several studies have identified potential indicators and screening targets for the early detection and diagnosis of ovarian serous papillary carcinoma to monitor presymptomatic aspects of the disease and disease progression [14-15] [36]. While there are currently no clinically established diagnostic tools using urinalysis or seranalysis, these experimentally and clinically identified targets can be categorized into two groups:

1. Biomarker proteins that are upregulated at least twofold or higher in metastatic over primary ovarian serous papillary carcinoma (such as EGFR, MUC1, Collagen Type I, TIMP-3, Fibronectin, Calreticulin) and 2. Biomarker proteins that are upregulated at least twofold or higher in primary over metastatic ovarian serous papillary carcinoma (such as apolipoprotein A-I, Complement component 7, mitogen activated protein kinase 13, Ryanodine Receptor).

This differentiation will ultimately allow the establishment of a temporally distinct diagnosis to aid in monitoring presymptomatic aspects of the disease, disease progression from primary to metastatic ovarian serous papillary carcinomas, and the efficacy of intervention therapies. By use of the GMR sensor system of the present invention, a set of commercially available specific antibodies and well-researched aptamers clinically relevant in the screening of ovarian cancer can be used to provide superior results other analysis techniques. These antibodies have been chosen based on following criteria:
1. Antibodies are from a renewable source, i.e. can be produced in large quantities without changes in functional properties;
2. Antibodies have a proven epitope specificity, i.e. recognize the targeted ovarian cancer biomarker and do not crossreact with other proteins or compounds;
3. Antibodies have high relevance for ovarian cancer, i.e. their targets are reliable biomarkers for ovarian cancer with a proven upregulation of at least two-fold or higher in patients with ovarian serous papillary carcinoma [14-15];
4. In addition to the properties described in criterion 3, antibodies have high relevance for unequivocally distinguishing ovarian cancer from other types of cancer and diseases and, equally important, for distinguishing between metastatic and primary ovarian serous papillary carcinoma [14-15]. This is primarily achieved by the capability to detect multiple targets' concentrations simultaneously.

The specificity in target recognition (criteria 2-4) is particularly relevant because ultimately the invention would allow expedient decisions on additional diagnostics and therapy choices for clinicians in the field.

In Vitro Model

Early validation testing has been performed using an in vitro model. In order to combine the highest possible clinical relevance with a financially viable research plan, the targeted in vitro models for ovarian cancer were chosen based on four criteria:
1. Cell lines are of human origin;
2. Cell lines had been derived directly from patients with ovarian cancer and are not from other types of cancer with ovarian side effects/metastases;
3. In vitro models are established (used by ovarian cancer researchers in peer-reviewed publications) and reproducible (available through the American Type Culture Collection (ATCC) or the National Institutes of Health (NIH));
4. Cells have been established and tested.

This rationale will allow us the most effective transition towards clinical samples (human serum, blood, plasma, etc.)

Cell Lines and Cell Culture

Human ovarian cancer lines of epithelial origin and of different stages (Table 2) were purchased from American Type Culture Collection (ATCC, Manassas, VA). Cells were grown in a humidified atmosphere of 37° C./5% CO2 and maintained according to the ATCC protocols. Cells were grown to approximately 75% confluency in 75 $cm^2$ (T75) tissue culture flasks with filtered caps (TPP, MidSci, St. Louis, MO) and split using 0.25% trypsin-2,2','',2'''-(ethane-1,2-diyldinitrilo) tetraacetic acid such that they would grow to 75% confluency within 48 hours. After at least three passages and exactly 48 hours after reseeding, supernatants were collected by aspiration, centrifuged for 1 minute at 300×g to collect any cell debris. The resultant supernatants were aliquoted in small volumes (1-5 mL) and stored frozen at −80° C. until used in the experiments. At the same time, cell pellets were collected by scraping the cells in 0.1M ice-cold phosphate-buffered saline pH 7.4 without calcium and magnesium (PBS; Lonza, Walkersville, MD).

TABLE 2

Cell lines used for the detection of biomarker proteins in ovarian carcinoma

| Name | description | source | ATCC catalog number | references |
|---|---|---|---|---|
| Caov-3 | Epithelial ovarian papillary adenocarcinoma | human | HTB-75 | [37] |
| SK-OV-3 | Epithelial ovarian moderately well-differentiated adenocarcinoma | human | HTB-77 | [38-39] |
| OVCAR-3 | Epithelial ovarian poorly differentiated papillary adenocarcinoma | human | HTB-161 | [40] |
| TOV-21G | Epithelial ovarian poorly differentiated primary malignant adenocarcinoma; Tumor stage: grade 3, stage IIIC | human | CRL-11730 | [41] |
| TOV-112D | Epithelial ovarian poorly differentiated primary malignant adenocarcinoma; tumor stage: grade 3, stage IIIC | human | CRL-11731 | [42] |

Antibodies and Standards

Tables 3 and 4 list the selective agents (antibodies) applied in this invention as well as the standard biomarker proteins used to quantify known levels in background buffer and/or cell culture media.

TABLE 3

Antibodies used for the detection of biomarker proteins in ovarian carcinoma

| Target | Manufacturer | Catalog # | Documented upregulation in primary or metastatic ovarian carcinoma | References |
|---|---|---|---|---|
| Fibronectin | RnD Systems | MAB1918 | metastatic | [43] |
| Apolipoprotein A1 | Gen Way Bio | 20-783-73037 | primary | [44-46] |
| Calreticulin | Assay Designs | SPA-601F | metastatic | [47-51] |
| Complement C7 | AbCam | Ab8791 | primary | [52] |
| Collagen Type I | AbCam Gen Way Bio | Ab34710 | metastatic | [53-57] |
| MAP Kinase 13 | Assay Designs | H00005603-M01 | primary | [58-62] |
| TIMP 3 | RnD Systems | MAB973 | metastatic | [63-66] |
| Ryanodine receptor | Millipore | MAB3086 | primary | [67-72] |

TABLE 3-continued

Antibodies used for the detection of biomarker proteins in ovarian carcinoma

| Target | Manufacturer | Catalog # | Documented up-regulation in primary or metastatic ovarian carcinoma | References |
| --- | --- | --- | --- | --- |
| Ryanodine receptor 2 | Millipore | AB9080 | | |
| Ryanodine receptor 3 | Millipore | AB9082 | | |

TABLE 4

Recombinant proteins used for the detection of biomarker proteins in ovarian carcinoma

| Target | Manufacturer | Catalog # |
| --- | --- | --- |
| Fibronectin | RnD Systems | 1918-FN-02M |
| Apolipoprotein A1 | GenWay Biotech | 11-783-79480 |
| Calreticulin | Assay Designs | SPA-600F |
| Collagen Type I | Genway Biotech | 11-511-248456 |
| MAP Kinase 13 | Genway Biotech | 10-782-55061 |
| TIMP 3 | RnD Systems | 973-TM-010 |
| Complement C7 | Abcam | |
| Ryanodine Receptor | Millipore or custom | |

Biosensor Activation and Performance Examples

Sensor elements are activated with commercially available silane chemistries, and cross-linking agents such that the selective (antibody or aptamer for example) layers can be attached to impart detection selectivity. Specifically, detection of biomarker proteins that are upregulated clinically at least twofold or higher in metastatic over primary ovarian serous papillary carcinoma (Collagen Type I, TIMP-3, Fibronectin, Calreticulin, EGFR, MUC1) and of biomarker proteins that are upregulated at least twofold or higher in primary over metastatic ovarian serous papillary carcinoma (apolipoprotein A-I, Complement component 7, mitogen activated protein kinase 13, Ryanodine Receptor) were be performed in cell culture supernatants, as well as serum. It is believed that the sensor systems can be pre-sensitized with activated sensor elements (with integrated antibody/aptamer detection layer), such that little or no processing is required for operation by the end user.

We have investigated several attachment chemistries in order to optimize antibody sensitivity and stability in this invention. Two different silane attachment chemistries for the antibody layers were the focus of the study. They include 3-Aminopropyltriethoxysilane (APS, Pierce) and carboxyethylsilanetriol sodium salt (CSS, Gelest).

Various concentrations of silanes were investigated (from 1% to 10%) to optimize the initial linker layer (APS or CSS) on the sensor element. For CSS, it was found that a 10% solution in DI water provided the largest resonant peak shift, thus indicating more available binding sites for antibody attachment. Since CSS deposits carboxyl groups on the sensors surface, 1-Ethyl-3-[3-dimethylaminopropyl]carbodiimide hydrochloride (EDC, Pierce) and N-hydroxy succinimide (NHS, Pierce) is used as a heterobifuntional crosslinker to link the carboxyl group on the sensor to amine groups on the antibody. In this process, a solution of 2 mM EDC and 5 mM NHS is prepared in phosphate buffered silane (PBS, pH 5.5). Immediately, the EDC/NHS solution is pipetted onto the sensor and incubated at 37° C. for 20 minutes. The sensor is aspirated and washed with PBS with TWEEN (wash buffer, pH 7.4) three times. The capture antibody is then incubated on the sensor surface for 2 hours at 37° C. For the APS, it was determined that a 6% solution in ethanol provided the largest resonant peak shift. Due to APS depositing amine group onto the sensor surface, a homobifunctional crosslinker, disuccinimidyl suberate (DSS, Pierce), is used to link the amine group from the sensor to an amine group on the antibody. For this process, the antibody is chemically attached to the amino-activated sensor surface using a 50 molar excess of the DSS to antibody. Equal volumes of antibody and DSS are pipetted onto the sensor and incubated at room temperature for 90 minutes. The sensor is aspirated and washed with PBS with TWEEN three times.

Figure 16:
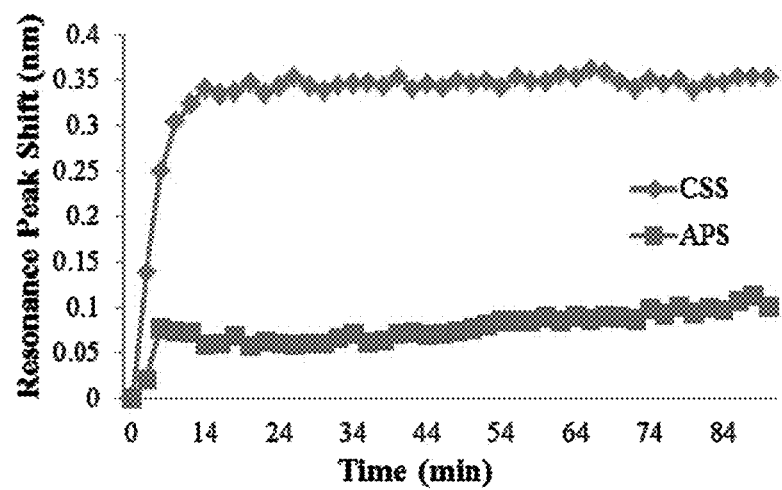
FIG. 16. (a) Real-time TM resonance peak kinetic binding of TIMP-3 antibody to silane activated sensor. (b) Total resonance TM shift of antibody binding to silane. TIMP-3 antibody binding to CSS-activated sensor gave an average shift of 353 pm with a standard deviation of 14 pm. TIMP-3 antibody binding to APS-activated sensor gave an average shift of 101 pm with a standard deviation of 7 pm. Experiment was run in triplicate with reference phosphate buffered saline (PBS) subtracted from data.
Figure 16:
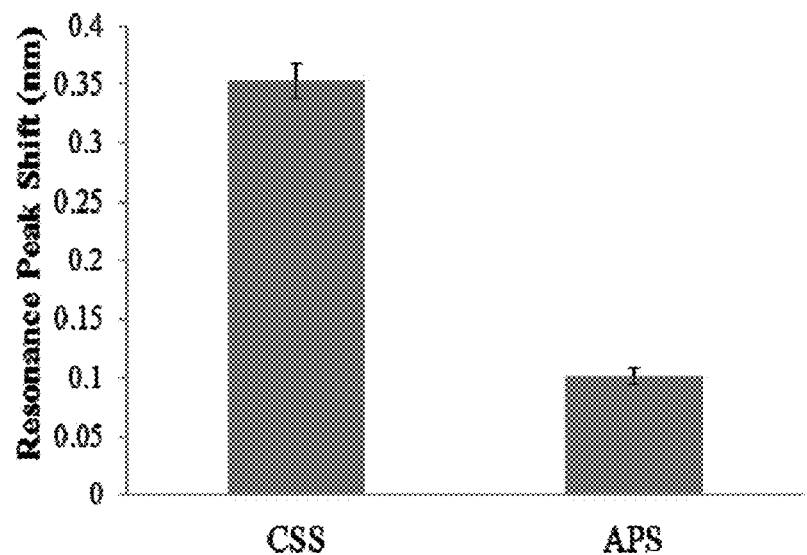

FIG. 16 illustrates the real-time binding of tissue inhibitor of metalloproteinase 3 (TIMP3) antibodies to the CSS and APS surfaces. Several concentrations of antibodies were investigated (from 1 µg/ml to 15 µg/ml in phosphate buffered saline) to determine the optimal concentration that provides the largest peak shift. It was found that 10 µg/ml concentration provided the best antibody packing density while minimizing steric hindrance for the CSS-activated sensor and 5 µg/ml antibody concentration for the APS-activated sensor.

Non-Specific Binding

Figure 17:
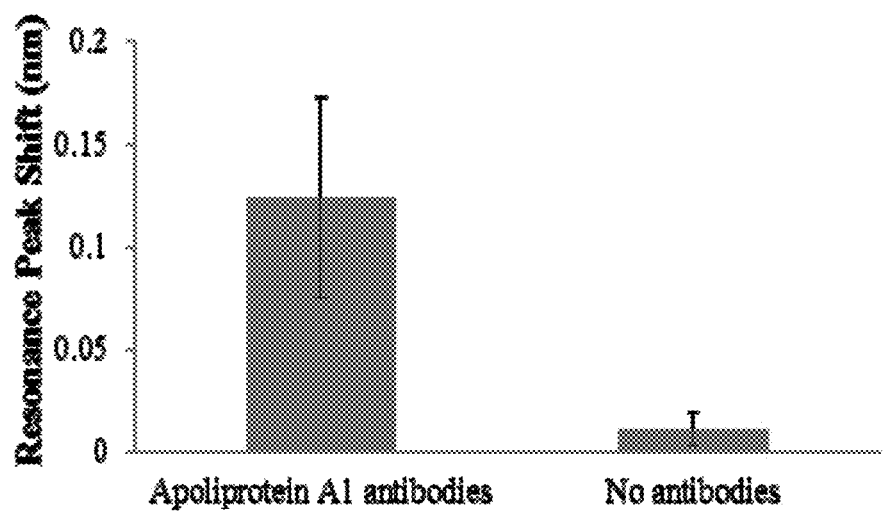
FIG. 17. (a) Comparison of the TM resonant peak shift due to the OVCAR-3 media test sample binding to the ApoA-1 antibodies on the sensors surface versus the non-specific binding on the sensor elements not coated with antibodies. Tests are run in quadruplicate and averaged. (b) Comparison of the TM resonant peak shift due to the serum test samples binding to the Fibronectin antibodies on the sensors surface versus the non-specific binding on the sensor elements not coated with antibodies. Tests are run in quadruplicate and averaged.
Figure 17:
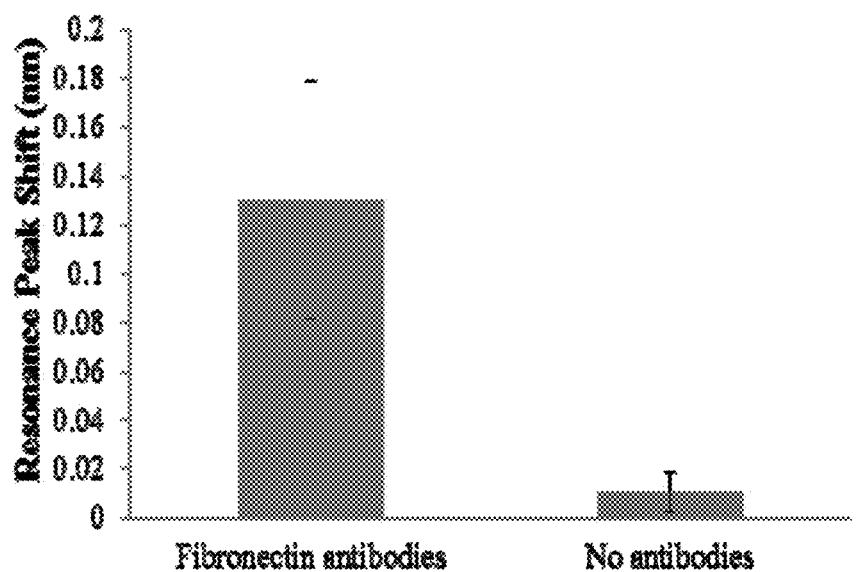

To investigate the amount of non-specific binding that might be occurring during the media/supernatant experiments, a negative reference well is prepared using a blocked silanized well (no antibodies attached) and compared to wells containing specific antibodies for Apolipoprotein A-1 (ApoA-1) and for Fibronectin. The capture antibodies for ApoA-1 and Fibronectin are monoclonal mouse antibodies that are chemically attached to the sensor surface using CSS chemistries. After antibody attachment, the unbound sites are blocked with a blocking buffer (Cayman Chemical, 1% Bovine Serum Albumin, BSA) for 30 minutes. OVCAR-3 media (having ApoA-1 and Fibronectin naturally present) is incubated in both the wells containing the specific antibodies, and the wells have no antibodies present. FIG. 17 illustrates the minimal shift results from the sample incubating on the negative reference well as compared to the well containing the specific antibodies. Results are based on the difference of initial and final PBS baseline readings and are repeated in quadruplicate and averaged.

Figure 18:
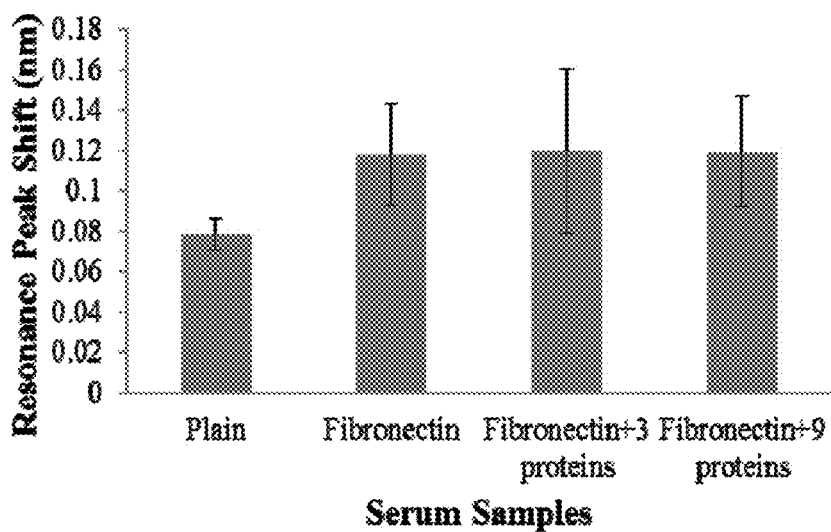
FIG. 18. Total resonance peak shift of Fibronectin in serum binding to corresponding antibody. The data illustrates the low non-specific binding that is measured when the sample contains other known concentrations of proteins.
Figure 19:
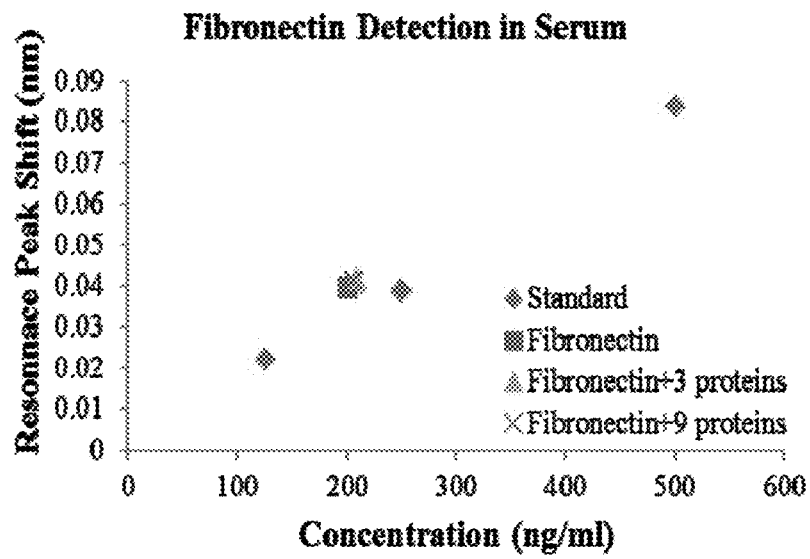
FIG. 19. A Fibronectin standard curve is shown in blue, and the doped serum samples are measured against the curve to give absolute values of Fibronectin detected. Based on the standard linearity curve of y=0.0002x+0.0003 ($R^2$=0.9955), it is determined that the serum doped with Fibronectin has a detected value of 199.9 ng/ml, the serum doped with Fibronectin plus 3 biomarker proteins has a value of 208.6 ng/ml, and the serum containing all 10 biomarker proteins has a Fibronectin concentration of 206.75 ng/ml. Plain serum is used as a negative reference and subtracted from the data. Results are based on difference of initial and final PBS baseline readings and are repeated in quadruplicate and averaged, with major outliers removed.

Since a particular application of in this invention is to test patient serum samples, we investigated the amount of non-specific binding that may occur in serum samples. Human male serum from AB plasma (Sigma) is used as the serum sample for the assay. Fibronectin concentrations are detected in pure serum; serum spiked with a known concentration of 250 ng/ml Fibronectin; serum spiked with known concentrations of Fibronectin (250 ng/ml), TIMP3 (500 ng/ml), MAPK13 (1 µg/ml), and ryanodine receptor (4 µg/ml); and serum spiked with known concentrations of all 10 biomarkers used for the ovarian panel employed in an embodiment of the present invention. The serum samples are incubated for 1 hour at 37° C. on the sensor elements. Measurements are based on difference of initial and final PBS baseline readings. FIGS. 18 and 19 illustrate the total resonant shift for the different serum samples. From these results, minimal nonspecific binding occurs due to the presence of other biomarker proteins.

In an effort to further minimize non-specific binding effects, Millipore's (Billerica, MA) CBS-K Super Chemiblock reagent was briefly investigated as a possible blocking agent (in lieu of standard BSA blocking agents). This reagent is added to the patient serum sample before testing occurs in order to bind to interfering antibodies in the sample [73]. It is believed Chemicon's reagents can help identify and minimize non-specific binding issues.

Spike and Recovery Samples

Figure 20:
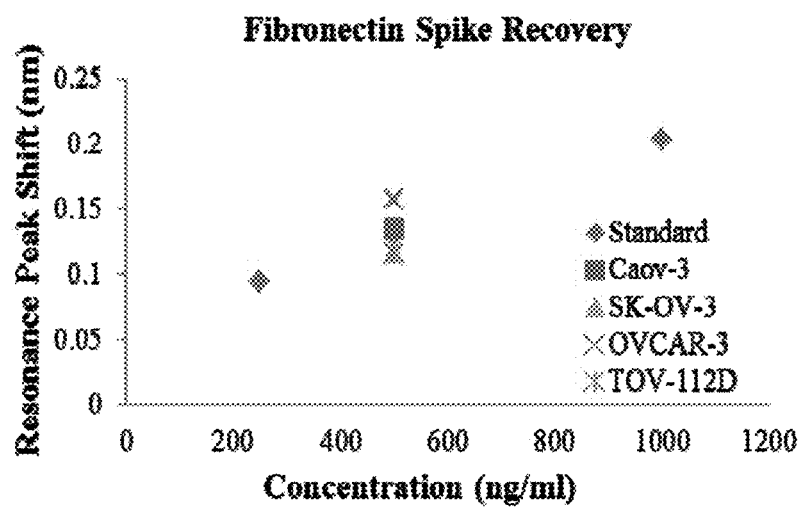
FIG. 20. (a) Fibronectin standard diluent resonance peak shift and standard curve (in blue) compared to the resonance peak for the spiked media solutions. Medias were spiked with 500 ng/ml Fibronectin protein. (b) Calreticulin standard diluent resonance peak shift and standard curve (in blue) compared to the resonance peak for the spiked media solutions (250 ng/ml calreticulin protein). Values reported for the spiked samples reflect the subtraction of the no-spike reference medias. Tests are run in quadruplicate and averaged.
Figure 20:
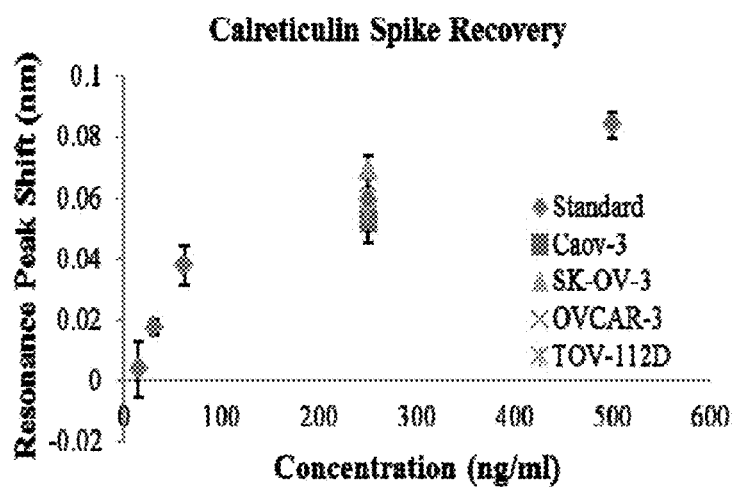

Since the cell supernatant and media samples are made up of complex matrices, we used spike and recovery for each biomarker protein assay to determine whether the protein detection is affected by a difference between the diluent (Cayman Chemical) used to prepare the standard curve and the media sample matrix. In the spike and recovery experiments, a known amount of protein standard is added to the sample matrix (corresponding growth media for each cell line) and compared to a standard curve measured in diluent [74]. The media and standard samples are then measured for protein attachment. The two sets of total resonance peak shift measurements are compared. If the values match, it is concluded the background matrix does not interfere with the protein detection. If the measurements differ, a separate concentration curve in the appropriate background must be performed. FIG. 20 shows spike and recovery experiments performed for Fibronectin and Calreticulin. Measurements are based on difference of initial and final baseline readings with pure reagent diluent or pure media used as negative controls and subtracted from the data. Since TOV-112D and TOV-21G are grown in the same media, only one media was compared against the standard curve for both cell lines.

TABLE 5

Fibronectin Spike and Recovery

| Medium | Spike Level (ng/ml) | Standard Diluent Resonance Peak Shift (nm) | Spiked Resonance Peak Shift (nm) | Recovery % |
|---|---|---|---|---|
| Caov-3 | 500 | 0.129 | 0.135 | 104.7 |
| SK-OV-3 | 500 | 0.129 | 0.117 | 90.7 |
| OVCAR-3 | 500 | 0.129 | 0.157 | 121.7 |
| TOV-112D | 500 | 0.129 | 0.116 | 89.9 |

TABLE 6

Calreticulin Spike and Recovery

| Medium | Spike Level (ng/ml) | Standard Diluent Resonance Peak Shift (nm) | Spiked Resonance Peak Shift (nm) | Recovery % |
|---|---|---|---|---|
| Caov-3 | 250 | 0.0600 | 0.0526 | 87.7 |
| SK-OV-3 | 250 | 0.0600 | 0.0692 | 115.3 |
| OVCAR-3 | 250 | 0.0600 | 0.0649 | 108.2 |
| TOV-112D | 250 | 0.0600 | 0.0543 | 90.5 |

Tables 5 and 6 illustrate the percent recoveries for the Fibronectin and Calreticulin spike-recovery assays. The percent recovery is calculated by comparison of the spiked resonance peak versus the standard diluent resonance peak. All values represent the average of four replicates from initial to final baseline readings, with major outliers removed.

Biomarker Protein Detection

Assay protocols have been developed and performed for detection of the panel of biomarker proteins using the angular-based GMR system developed in FIG. 10 and the spectroscopic system shown in FIG. 15. All angular-based tests are performed at room temperature and without thermal control. In these experiments, the TM polarization resonance is tracked during detection (unless otherwise noted).

For assays utilizing antibodies as the detection layer, GMR sensor plates are coated with a commercially available silane, CSS or APS (as described in the chemistry optimization section above), which provides a means to covalently bond the antibody to the sensor surface. The specific antibody for each biomarker protein is immobilized on the sensor using the crosslinking agents. To minimize nonspecific binding, the plate is blocked using a 1% bovine serum albumin solution (Cayman Chemical). To generate a standard curve, dilutions of standard protein are prepared using reagent diluent containing 1% BSA (eBioscience). Neat reagent diluent is used as a baseline measurement and blank reference. Spike and recovery samples are run for each assay performed, with each cell line's media having a known spiked protein and compared to the standard value in reagent diluent. This ensures the supernatant/media sample's matrix is not interfering with the detection of the protein. All ovarian carcinoma cell media and supernatant samples are testing unprocessed, with no sample preparation, unless stated otherwise. All samples are incubated on the prepared sensor surfaces for 60 minutes (unless otherwise stated) at 37° C., and then they are washed with PBS/Tween to remove unbound material and subsequently measured on the GMR system. Results on all protein detection data are based on difference of initial and final baseline readings and are repeated in quadruplicate and averaged, with major outliers removed.

Figure 21:
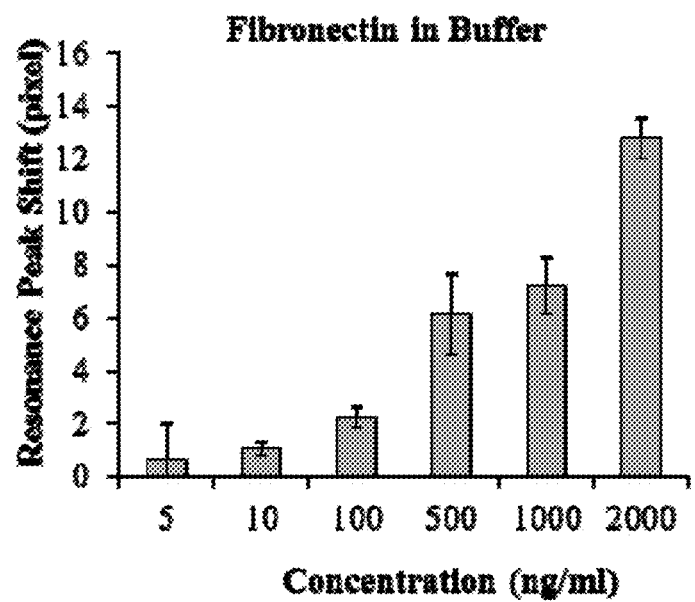
FIG. 21. (a) Experimental sensing results for detection of known concentrations of Fibronectin in buffer. (b) Resonance peak shift response for detection of known concentrations of Fibronectin in cell culture media (2-hour incubation). Neat cell medium is used as a reference and subtracted from measured data. All results are repeated in triplicate (outliers are removed) and averaged. The limit of detection in this experiment is approximately 10 ng/ml for Fibronectin.
Figure 21:
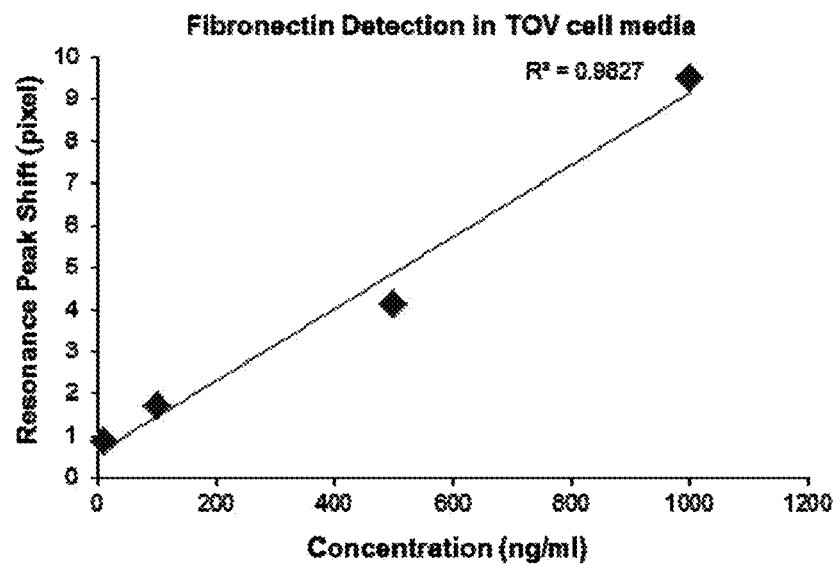
Figure 22:
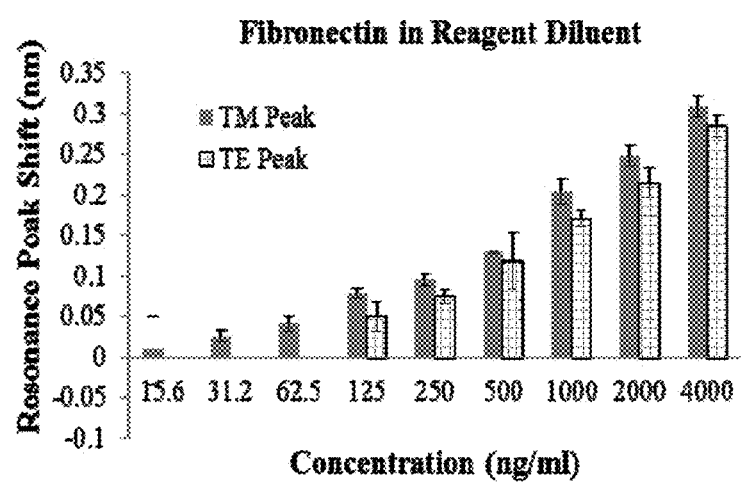
FIG. 22. (a) Total resonance peak wavelength shift of Fibronectin binding to capture antibody on the sensor surface for a concentration range from 15.6 ng/ml to 4 µg/ml. Both TE and TM polarization resonances are tracked. (b) Caov-3 supernatant (green) and media (red) sample resonance shifts are compared to the known concentration resonance shifts (standard curve in blue) to obtain Fibronectin concentrations. All measurements are repeated in quadruplicate and averaged.
Figure 22:
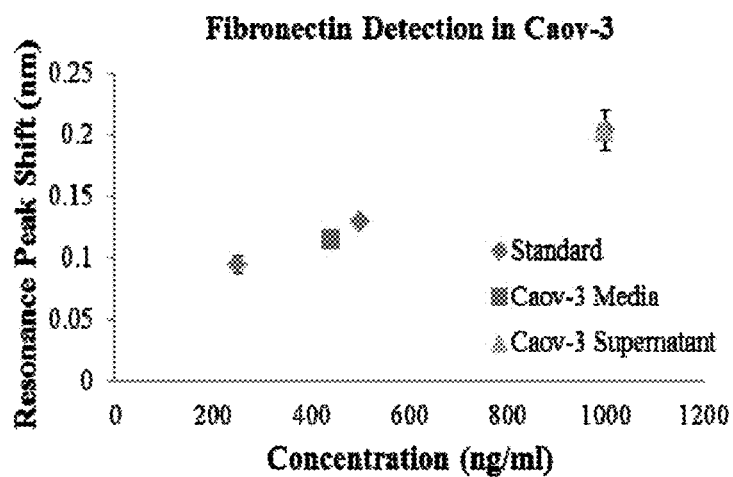

In an embodiment, a protocol has been developed for detection of the biomarker protein Fibronectin. The capture antibody used to impart sensor specificity is a monoclonal antibody specific to Fibronectin. FIG. 21 illustrates the measured resonance peak shifts after binding of Fibronectin to the capture antibody specific for this protein. In FIG. 21(a), dilutions of the Fibronectin protein are prepared in PBS and the detection response is measured after incubating for 2 hours on the sensor element. While the detection is monitored in real time, the final incubation time varies depending on binding dynamics, which slow down when the room is cooler. In FIG. 21(b) the experiment is repeated with dilutions in a background of cell culture media. A standard curve fit was generated with a good fit value (coefficient of determination $R^2$~0.98). The limit of detection for the assay performed in FIG. 21 is <10 ng/ml. Selectivity for experiments performed in FIG. 21 was imparted utilizing APS attachment chemistries (described above). In FIG. 22, standard dilutions of the Fibronectin protein are prepared in reagent diluent and measured after a 1-hour incubation. FIG. 22(a) tracks resonance peak changes for both TE and TM polarizations. In this experiment, the TM resonance is slightly more sensitive than the TE resonance peak; however, both trend in response similarly. The limit of detection for this assay is ~20 ng/ml. It is observed that the spectroscopic system is slightly less sensitive than the angular prototype. This is due to the capability to optimize sensitivity/dynamic range on the imaging camera when using the angular detection scheme. In the spectroscopic system, there are detection limitations imposed by the chosen optical spectrum analyzer. However, by utilizing a more expensive analyzer, an increased sensitivity can be readily obtained.

FIG. 22(b) illustrates Fibronectin detected in Caov-3 media and supernatant. The TM resonance peak shift for the test sample (unknown) is compared to the standard concentration (known) to obtain a measured concentration of 439.1 ng/ml for Caov-3 media and 996.7 ng/ml for Caov-3 supernatant. Table 7 shows the Fibronectin concentration detected for each cell line supernatant and media.

TABLE 7

Fibronectin Detection in Media and Supernatant

| Cell Line | Protein Concentration in Media (µg/ml) | Protein Concentration in Supernatant (µg/ml) |
|---|---|---|
| Caov-3 | 0.439 | 0.997 |
| SK-OV-3 | 0.665 | 1.247 |
| OVCAR-3 | 1.430 | 1.730 |
| TOV-21G | 1.145 | 0.875 |
| TOV-112D | 1.145 | 1.185 |

Figure 23:
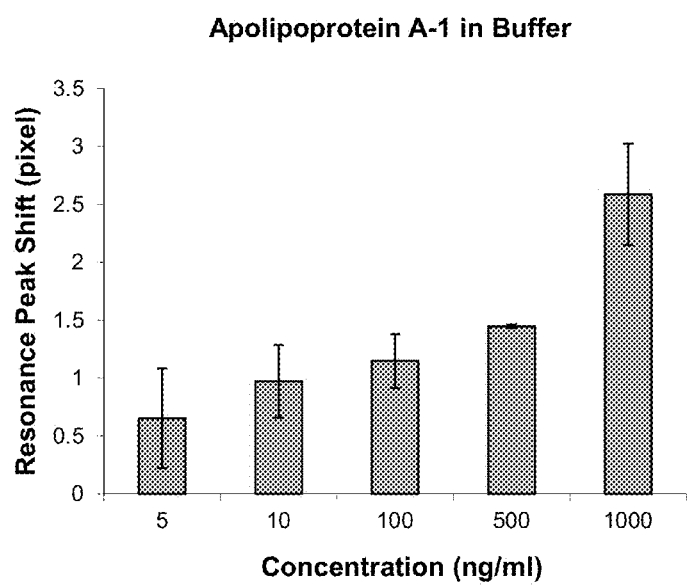
FIG. 23. Measured GMR sensor peak shift versus concentration for the detection of Apolipoprotein A-1 in buffer (2-hour incubation). Buffer is used as a reference and subtracted from data. All results are repeated in triplicate (outliers are removed) and averaged. In this experiment, the antibodies were chemically attached to the sensor element utilizing APS silane chemistries.
Figure 24:
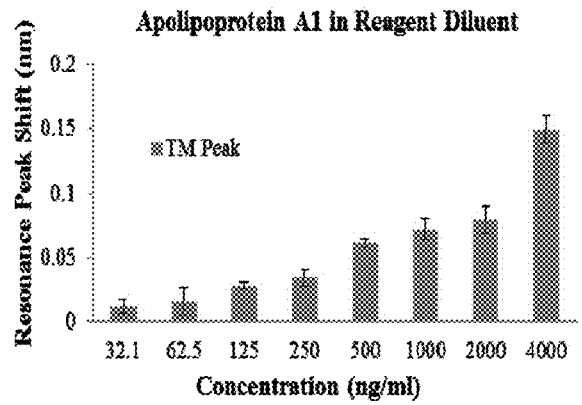
FIG. 24. (a) Total resonance peak wavelength shift of ApoA-1 binding to capture antibody on the sensor surface. (b) TOV-21G supernatant and media sample resonance shifts are compared to the known standard concentration resonance shifts. The detected ApoA-1 level in TOV-21G supernatant is 89 ng/ml and media is 59 ng/ml, showing only a slight secretion of protein in the ovarian cancer cell supernatant. All measurements are repeated in quadruplicate and averaged.
Figure 24:
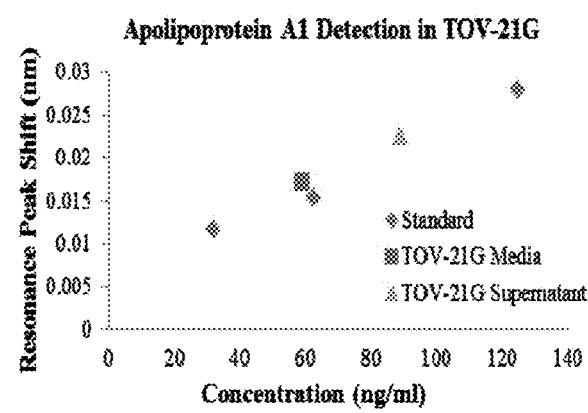

The detection of the biomarker protein Apolipoprotein A-1 (ApoA-1) in cell supernatant and media was performed by using a monoclonal mouse antibody (GenWay Biotech Inc, San Diego, CA) specific to ApoA-1. Dilutions of the standard ApoA-1 proteins (GenWay Bio) are prepared using reagent diluent to obtain the desired concentrations. Neat reagent diluent is used as a reference blank. FIG. 23 depicts the measured resonance peak shifts after binding of ApoA-1 to the capture antibody specific for this protein. In FIG. 23, dilutions of the ApoA-1 protein are prepared in buffer and the detection response measured after incubating for 2 hours on the sensor element. The limit of detection for this assay is approximately 5 ng/ml. FIG. 24(a) illustrates the measured resonance peak shifts for a standard dilution of ApoA-1 in reagent diluent. FIG. 24(b) illustrates cell line TOV-21G media and supernatant detected value tested against the standard curve at full concentration (no sample dilution). The TM resonance peak shift for the test sample (unknown) is compared to the standard concentration (known) to obtain a measured concentration using the standard linearity curve of y=0.0002x+0.0052 ($R^2$=0.989). Table 8 shows the ApoA-1 concentration detected for each cancer cell line supernatant and media.

TABLE 8

Apolipoprotein A-1 Detection in Media and Supernatant

| Cell Line | Protein Concentration in Media (µg/ml) | Protein Concentration in Supernatant (µg/ml) |
|---|---|---|
| Caov-3 | 0.064 | 0.044 |
| SK-OV-3 | 0.074 | 0.024 |
| OVCAR-3 | 1.380 | 1.350 |
| TOV-21G | 0.059 | 0.089 |
| TOV-112D | 0.059 | 0.229 |

Figure 25:
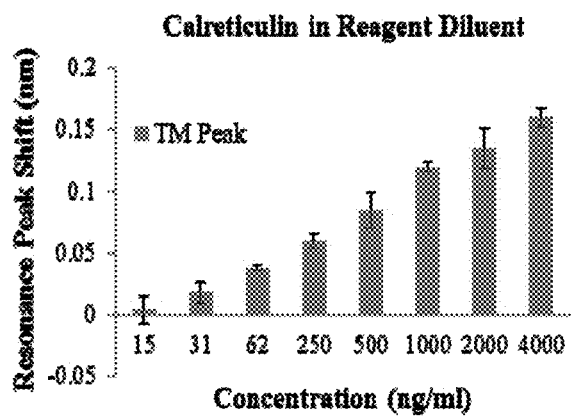
FIG. 25. (a) Total TM resonance peak wavelength shift of calreticulin binding to capture antibody on the sensor surface for a concentration range from 15.6 ng/ml to 4 µg/ml. (b) Diluted Caov-3 supernatant and media sample resonance shifts plotted with known standard protein concentrations.
Figure 25:
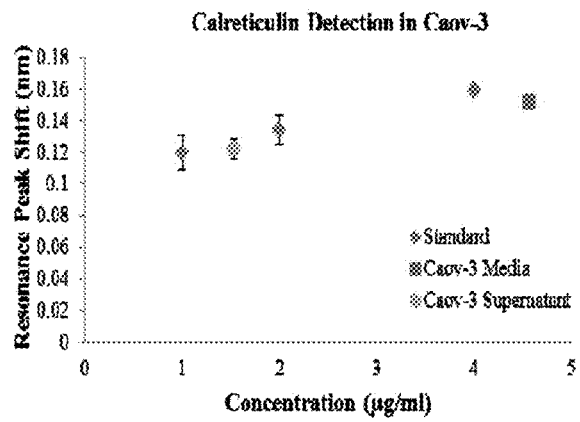

The calreticulin assay developed uses a monoclonal mouse antibody (Enzo Life Sciences, Plymouth Meeting, PA) specific to calreticulin. Standard calreticulin (Enzo Life Sciences) dilutions are prepared using reagent diluent to obtain the desired concentrations. For the cell supernatant and media samples, a 1:10 dilution in reagent diluent was employed, since the samples naturally contain high levels of calreticulin protein. However, preferably, the least amount of dilutent would be used. FIG. 25(a) illustrates the measured resonance peak shifts after binding of calreticulin to the capture antibody specific for the protein. FIG. 25(b) illustrates cell line Caov-3 media and supernatant detected value tested against the standard curve at a 1:10 dilution. The TM resonance peak shift for the test sample (unknown) is compared to the standard concentration (known) to obtain a measured concentration using the standard linearity curve of y=0.0132x+0.1069 ($R^2$=0.9986). The concentration of the diluted Caov-3 media is calculated to be 45.6 µg/ml and Caov-3 supernatant is 15.3 µg/ml (taking into consideration the dilution factor). Table 9 shows the final calreticulin concentrations detected for each cancer cell line supernatant and media.

TABLE 9

Calreticulin Detection in Media and Supernatant

| Cell Line | Protein Concentration in Media (µg/ml) | Protein Concentration in Supernatant (µg/ml) |
|---|---|---|
| Caov-3 | 45.60 | 15.33 |
| SK-OV-3 | 7.14 | 4.94 |
| OVCAR-3 | 47.37 | 50.30 |
| TOV-21G | 35.53 | 27.93 |
| TOV-112D | 35.53 | 0.96 |

Figure 26:
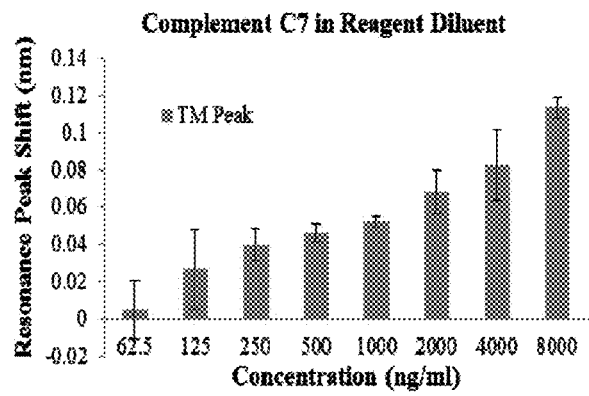
FIG. 26. (a) Total TM resonance peak wavelength shift of complement C7 binding to capture antibody on the sensor surface for a concentration range. (b) Caov-3 supernatant and media sample resonance shifts plotted with known standard protein concentrations. Using the standard linearity equation, it is determined that the complement C7 level in Caov-3 supernatant is 480 ng/ml and media is 730 ng/ml.
Figure 26:
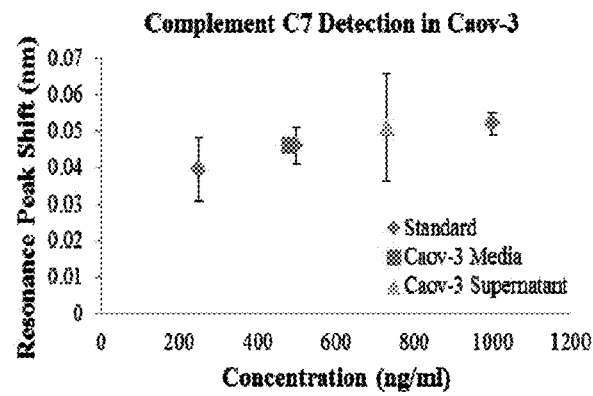

For the complement component 7 (complement C7) assay developed, a polyclonal sheep antibody (Abcam) specific to complement C7 is used to activate the sensor with a specific capture layer. A complement C7 peptide (Abcam) is used as a standard, and dilutions are prepared using reagent diluent to obtain the desired concentrations. Neat reagent diluent is used as a reference blank. The ovarian cancer cell supernatant and media samples are tested pure, with no sample preparations needed. FIG. 26(a) illustrates the measured resonance peak shifts after binding of complement C7 to the capture antibody specific for the protein. FIG. 26(b) illustrates cell line Caov-3 media and supernatant detected value tested against the standard curve at full concentration (no sample dilution). Table 10 shows the complement C7 concentration detected for each cancer cell line supernatant and media.

TABLE 10

Complement C7 Detection in Media and Supernatant

| Cell Line | Protein Concentration in Media (µg/ml) | Protein Concentration in Supernatant (µg/ml) |
|---|---|---|
| Caov-3 | 0.480 | 0.730 |
| SK-OV-3 | 1.430 | 1.030 |
| OVCAR-3 | 0.294 | 0.254 |
| TOV-21G | 0.630 | 0.580 |
| TOV-112D | 0.630 | 0.730 |

Figure 27:
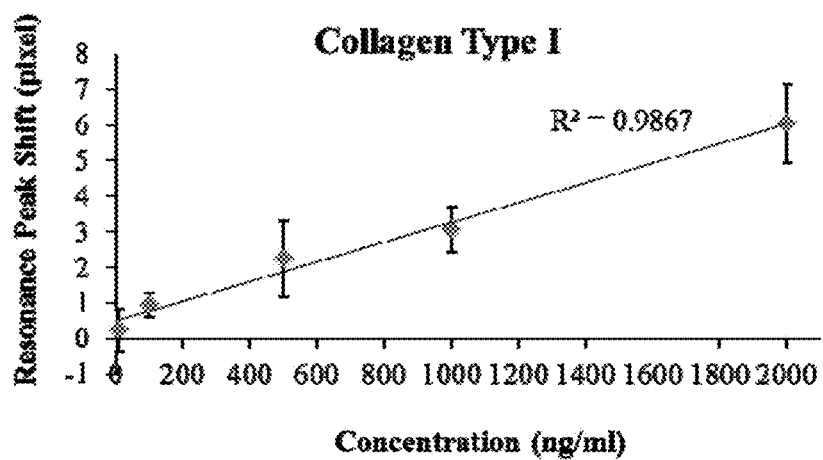
FIG. 27. Measured GMR sensor peak shift versus concentration for the detection of Collagen Type I in buffer after a 45-minute incubation. Neat buffer is used as a reference and subtracted from measured data. All results are repeated in triplicate (outliers are removed) and averaged. In this experiment, antibodies were chemically attached to the sensor element utilizing APS silane chemistries. The limit of detection for this assay was ~10 ng/ml.
Figure 28:
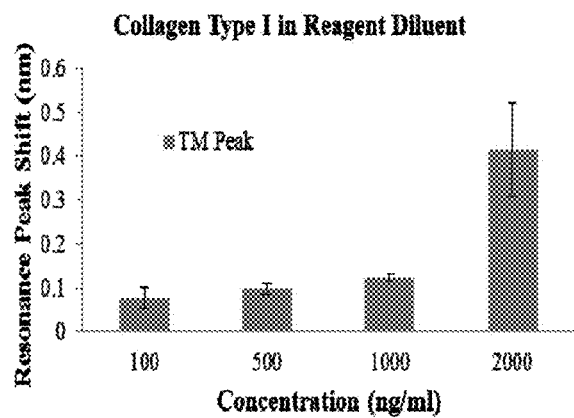
FIG. 28. (a) Resonance peak wavelength shift of collagen binding to capture antibody on the sensor surface. (b) SK-OV-3 supernatant and media sample resonance shifts are compared to the standard concentration resonance shifts to obtain supernatant/media collagen concentrations. All measurements are repeated in quadruplicate and averaged.
Figure 28:
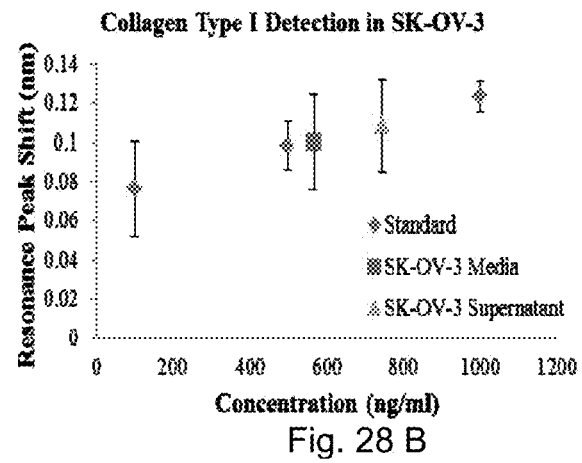

The Collagen type I assay is developed using a monoclonal antibody (GenWay BioTech) and standard Collagen type I protein (GenWay BioTech). FIG. 27 depicts the measured resonance peak shifts after binding of Collagen type I to the capture antibody specific for this protein. In FIG. 27, dilutions of the biomarker protein are prepared in buffer and the detection response measured after incubating for 45 minutes on the sensor element. The limit of detection for this assay is approximately 10 ng/ml. For FIG. 28, the standard protein is diluted to the working concentrations with reagent diluent, with neat reagent diluent used as a negative reference. FIG. 28(a) illustrates the total resonance peak shift of collagen in reagent diluent binding to its matched antibody for targeted protein levels of 0.1-2 μg/ml. FIG. 28(b) illustrates cell line SK-OV-3 supernatant and media concentrations compared to the collagen standard curve. It is determined that for SK-OV-3, the supernatant collagen concentration is 746 ng/ml and the media value is 566 ng/ml. Table 11 shows the collagen type I concentration detected for each cancer cell line supernatant and media.

TABLE 11

Collagen Type I Detection in Media and Supernatant

| Cell Line | Protein Concentration in Media (μg/ml) | Protein Concentration in Supernatant (μg/ml) |
|---|---|---|
| Caov-3 | 0.326 | 0.306 |
| SK-OV-3 | 0.566 | 0.746 |
| OVCAR-3 | 0.606 | 0.706 |
| TOV-21G | 0.607 | 0.906 |
| TOV-112D | 0.607 | 0.186 |

Figure 29:
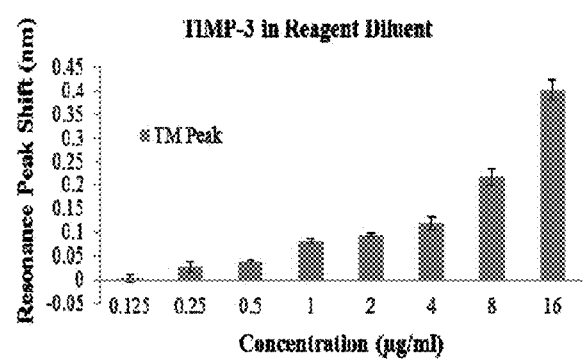
FIG. 29. (a) Total resonance peak wavelength shift of the biomarker TIMP-3 after binding to the capture antibody on the sensor surface. (b) SK-OV-3 supernatant and media sample resonance shifts are compared to the known standard concentration resonance shifts. The detected TIMP-3 level in SK-OV-3 supernatant is 472 ng/ml and media is 427.5 ng/ml, showing only a slight secretion of protein in the ovarian cancer cell supernatant. All measurements are repeated in quadruplicate and averaged.
Figure 29:
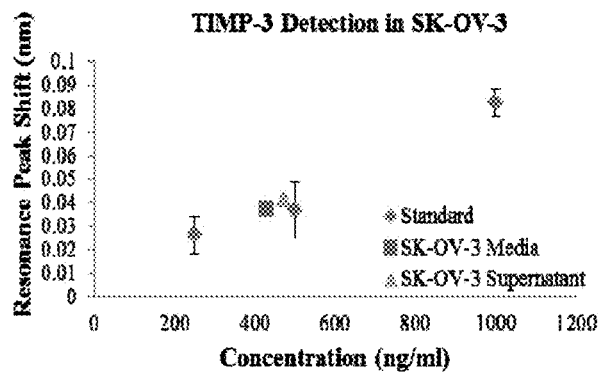

The detection of the biomarker protein tissue inhibitor of metalloproteinases 3 (TIMP-3) in cell supernatant and media was performed by using a monoclonal mouse antibody (R&D Systems) specific to TIMP-3. Dilutions of the standard TIMP-3 proteins (R&D Systems) are prepared using reagent diluent to obtain the desired concentrations. Neat reagent diluent is used as a reference blank. The ovarian carcinoma cell supernatant and media samples are tested pure, with no sample preparations needed. FIG. 29(a) illustrates the measured resonance peak shifts after binding TIMP-3 to the capture antibody specific for the protein. FIG. 29(b) illustrates cell line SK-OV-3 media and supernatant detected value tested against the standard curve. The TM resonance peak shift for the test sample (unknown) is compared to the standard concentration (known) to obtain a measured concentration using the standard linearity curve of $y=8E-05x+0.0037$ ($R^2=0.9766$). Table 12 shows the TIMP-3 concentration detected for each cancer cell supernatant and media.

TABLE 12

TIMP-3 Detection in Media and Supernatant

| Cell Line | Protein Concentration in Media (μg/ml) | Protein Concentration in Supernatant (μg/ml) |
|---|---|---|
| Caov-3 | 0.050 | 0.048 |
| SK-OV-3 | 0.427 | 0.472 |
| OVCAR-3 | 1.700 | 2.610 |
| TOV-21G | 0.050 | 0.293 |
| TOV-112D | 0.050 | 0.253 |

Known standards (blue) are measured to obtain a calibration curve that is used to quantify TOV-112D supernatant and media protein concentrations. Samples are ran in quadruplicate and averaged, with major outliers removed.

TABLE 13

Ryanodine Receptor Detection in Media and Supernatant

| Cell Line | Protein Concentration in Media (μg/ml) | Protein Concentration in Supernatant (μg/ml) |
|---|---|---|
| Caov-3 | 1.130 | 0.290 |
| SK-OV-3 | 4.480 | 0.054 |
| OVCAR-3 | 0.262 | 0.115 |
| TOV-21G | 2.956 | 2.658 |
| TOV-112D | 2.956 | 4.637 |

Figure 30:
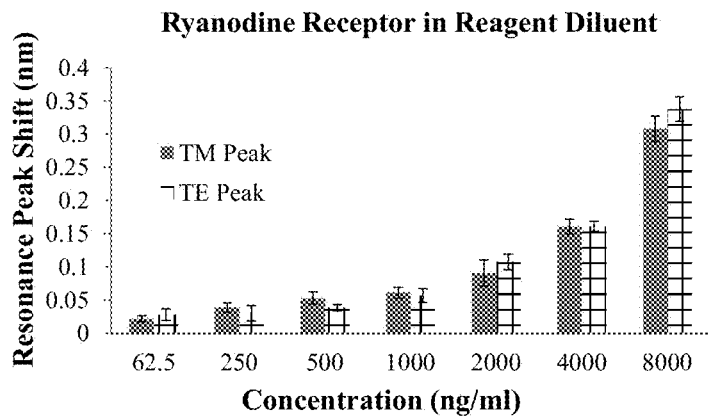
FIG. 30. (a) Resonance peak shift as a function of concentration for ryanodine receptor binding to detection antibody. Both TE and TM polarization resonances are tracked. (b) Resonance peak shifts for detection of ryanodine receptor.
Figure 30:
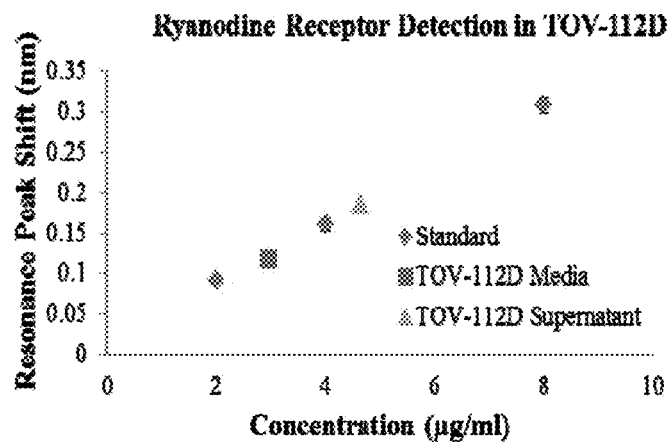

For the ryanodine receptor assay, the standard protein is custom made. The protein is from a mouse whole brain endoplasmic reticulum. A monoclonal mouse antibody (Millipore) specific for ryanodine receptor is applied to impart selectivity in this assay. Dilutions of ryanodine receptor are prepared in reagent diluent. FIG. 30(a) illustrates the measured resonance peak shifts after binding of ryanodine receptor to the capture antibody specific for this protein. FIG. 30(b) illustrates cell line TOV-112D media and supernatant detected value tested against the standard curve at full concentration (no sample dilution). The resonance peak shift for the test sample (unknown) is compared to the standard concentration (known) to obtain a measured concentration of 2.95 μg/ml for TOV-112D media and 4.63 μg/ml for TOV-112D supernatant. Table 13 shows the ryanodine receptor concentration detected for each cell line supernatant and media.

Figure 31:
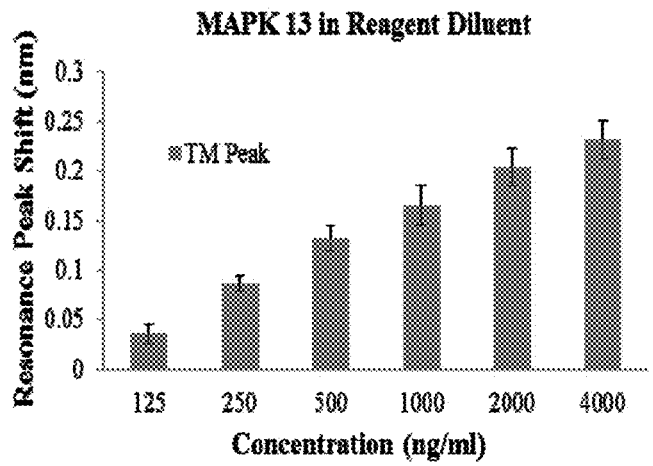
FIG. 31. Total resonance peak wavelength shift of MAPK 13 binding to capture antibody on the sensor surface for a concentration range of 125 ng/ml to 4 µg/ml.
Figure 32:
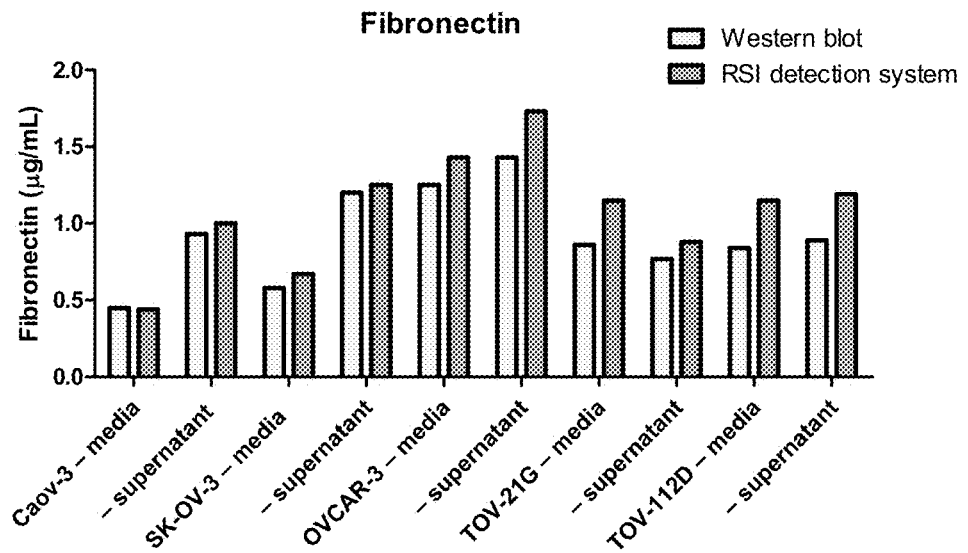
FIG. 32. (a) A summarized comparison of measured Fibronectin levels in cell culture media and supernatant samples using the GMR detection system and Western blot analysis. (b) Measured relative protein levels that are normalized with respect to the media control. Measurements were performed using the GMR detection system and compared with Western blot with good agreement.
Figure 32:
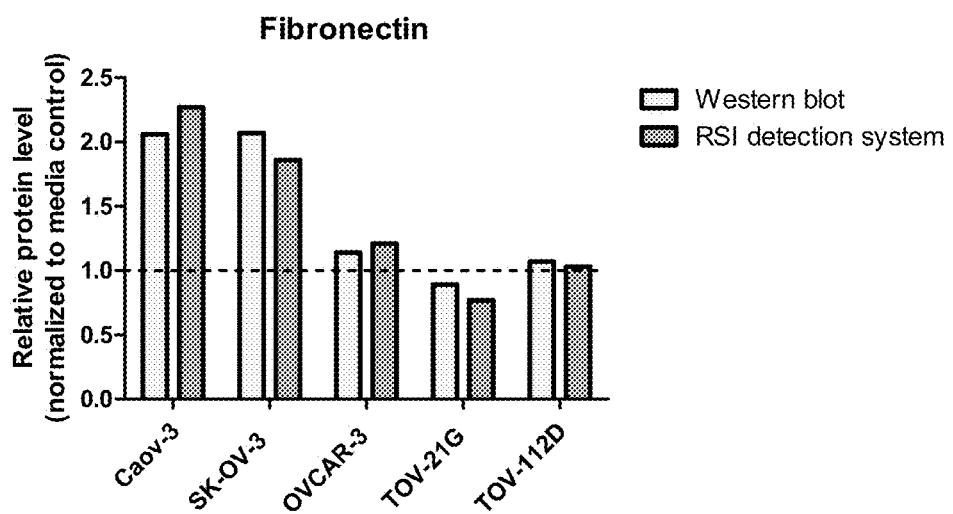
Figure 33:
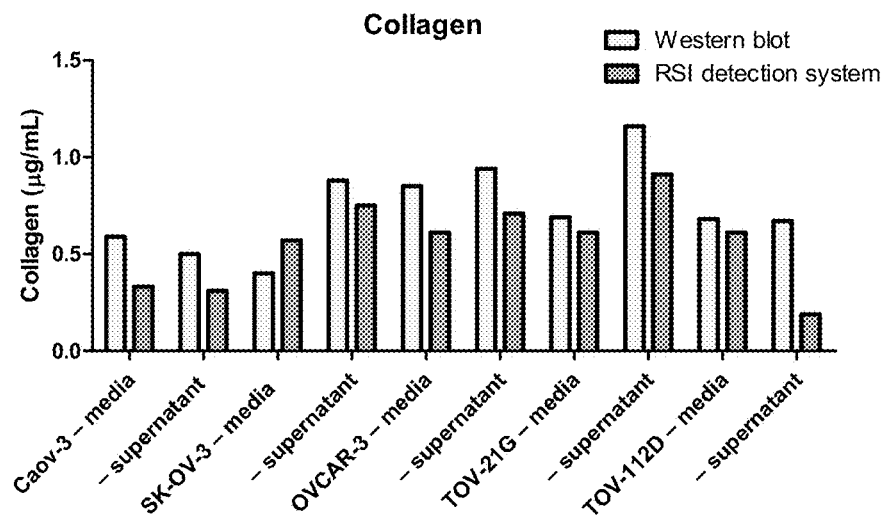
FIG. 33. (a) A summarized comparison of measured Collagen levels in cell culture media and supernatant samples using the GMR detection system and Western blot analysis. (b) Measured relative protein levels that are normalized with respect to the media control. Measurements were performed using the GMR detection system and compared with Western blot with good agreement.
Figure 33:
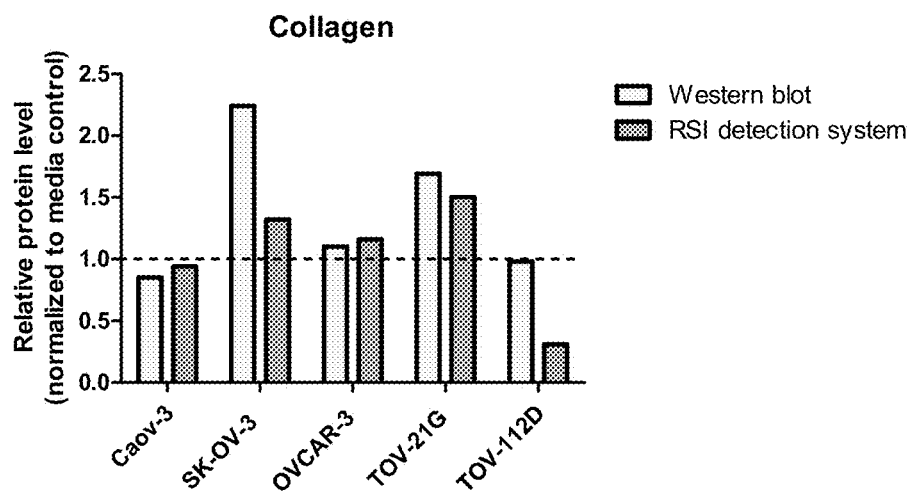
Figure 34:
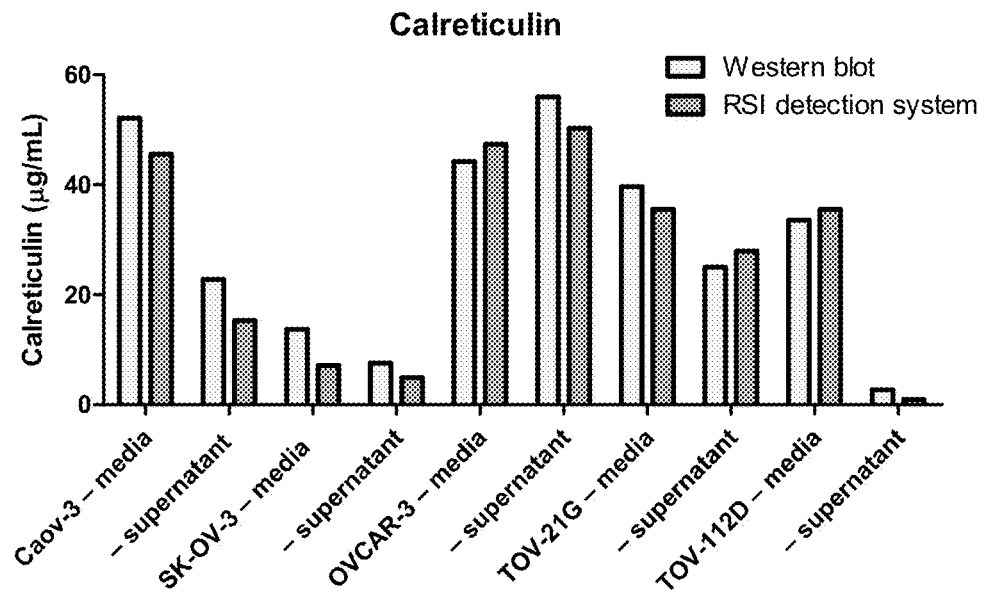
FIG. 34. (a) A summarized comparison of measured Calreticulin levels in cell culture media and supernatant samples using the GMR detection system and Western blot analysis. (b) Measured relative protein levels that are normalized with respect to the media control. Measurements were performed using the GMR detection system and compared with Western blot with good agreement.
Figure 34:
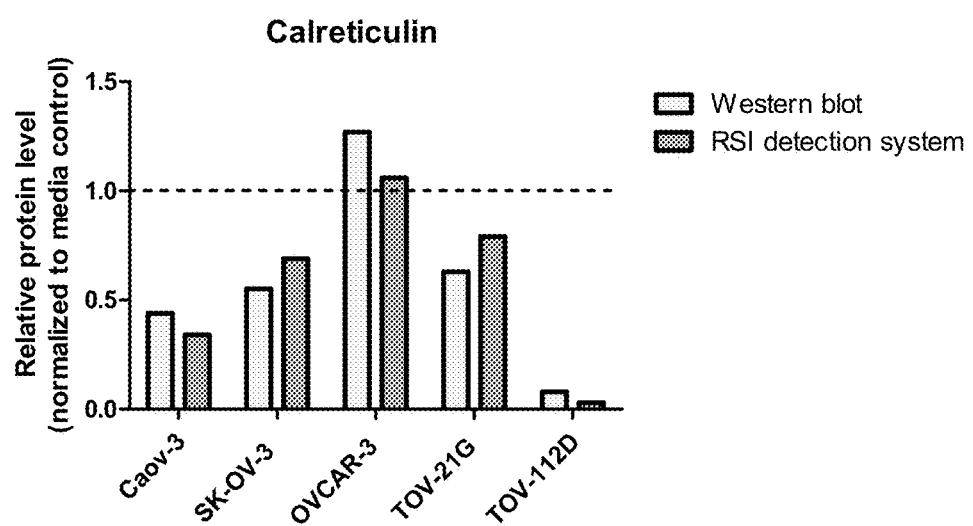
Figure 35:
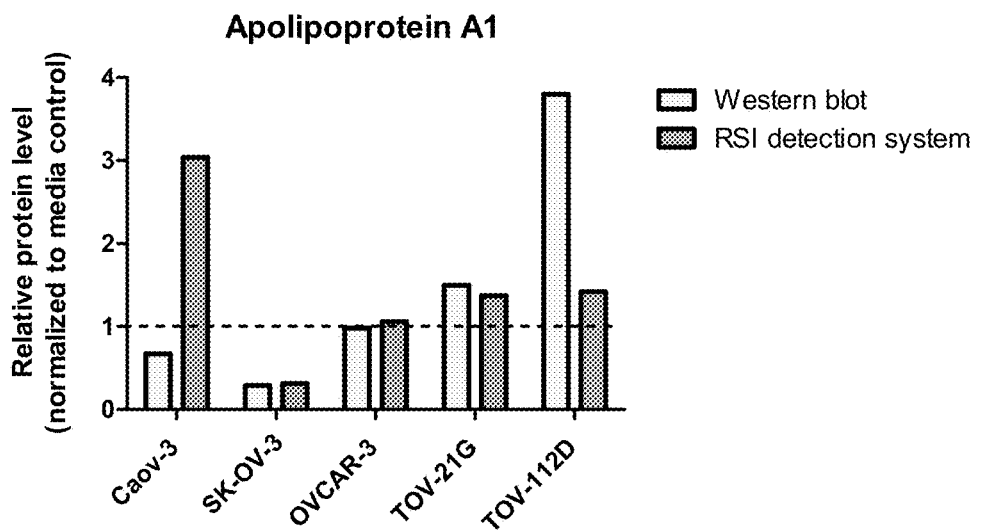
FIG. 35. (a) Measured relative protein levels for Apolipoprotein A-1 that are normalized with respect to the media control. Measurements were performed using the GMR detection system and compared with Western blot with good agreement. (b) Measured relative protein levels for Complement C7 that are normalized with respect to the media control. Measurements were performed using the GMR detection system and compared with Western blot with good agreement.
Figure 35:
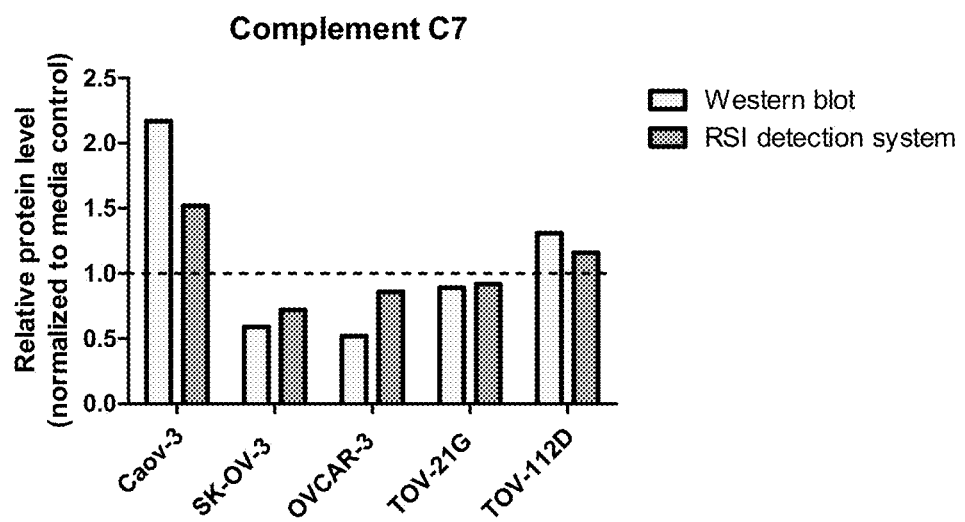
Figure 36:
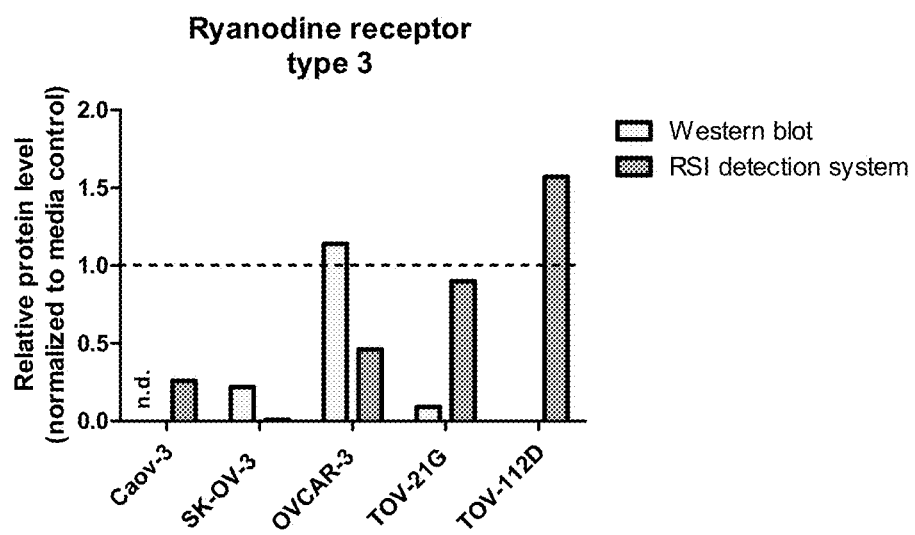
FIG. 36. Measured relative protein levels for Ryanodine receptor type 3 that are normalized with respect to the media control. Measurements were performed using the GMR detection system and compared with Western blot.

The mitogen activated protein kinase 13 (MAPK 13) assay was developed using a monoclonal antibody (Abnova) and protein (GenWay Bio). The standard protein is diluted in reagent diluent to yield the desired concentrations. Neat reagent diluent is used as a reference blank. FIG. 31 illustrates the measured resonance peak shifts after binding MAPK 13 to the capture antibody specific for the protein. MAPK 13 was detected in reagent diluent, but no protein was detected in any of the cell supernatants or media, including the spike and recovery samples. This could be due to the cell media/supernatant interfering with the antibodies on the sensor surface, thus preventing MAPK 13 detection.

Table 14 summarizes the absolute biomarker protein levels in the supernatant and media samples for all the ovarian carcinoma cell lines. Table 15 lists the relative levels of protein secretion into supernatant compared to media. Secretion (as defined as >1.5-fold increase in protein in supernatant compared with media) is highlighted in bold. Values larger than 1 suggest release; values smaller than 1 suggest uptake or degradation.

TABLE 14

Absolute protein levels (μg/ml) in media and supernatant

| Cell line | | Fibronectin | Apolipo-protein AI | Calreticulin | Complement C7 | Collagen Type I | MAP Kinase 13 | TIMP3 | Ryanodine receptor | EGFR | MUC1 |
|---|---|---|---|---|---|---|---|---|---|---|---|
| Caov-3 | Media | 0.44 | 0.06 | 45.60 | 0.48 | 0.33 | n.d. | 0.05 | 1.13 | 0.11 | n.d. |
| | Supernatant | 1.00 | 0.04 | 15.33 | 0.73 | 0.31 | n.d. | 0.05 | 0.29 | 0.14 | n.d. |
| SK-OV-3 | Media | 0.67 | 0.07 | 7.14 | 1.43 | 0.57 | n.d. | 0.43 | 4.48 | 0.40 | n.d. |
| | Supernatant | 1.25 | 0.02 | 4.94 | 1.03 | 0.75 | n.d. | 0.47 | 0.05 | 0.12 | n.d. |
| OVCAR-3 | Media | 1.43 | 1.38 | 47.38 | 0.29 | 0.61 | n.d. | 1.70 | 0.26 | 1.12 | n.d. |
| | Supernatant | 1.73 | 1.35 | 50.30 | 0.25 | 0.71 | n.d. | 2.61 | 0.12 | 0.14 | n.d. |
| TOV-21G | Media | 1.15 | 0.06 | 35.53 | 0.63 | 0.61 | n.d. | 0.05 | 2.96 | 0.43 | n.d. |
| | Supernatant | 0.88 | 0.09 | 27.92 | 0.58 | 0.91 | n.d. | 0.29 | 2.66 | 0.77 | n.d. |
| TOV-112D | Media | 1.15 | 0.06 | 35.53 | 0.63 | 0.61 | n.d. | 0.05 | 2.96 | 0.44 | n.d. |
| | Supernatant | 1.19 | 0.23 | 0.96 | 0.73 | 0.19 | n.d. | 0.25 | 4.64 | 0.66 | n.d. |

*n.d.—not detectable

TABLE 15

Relative protein levels in media and supernatant

| Cell line | Fibronectin | Apolipoprotein AI | Calreticulin | Complement C7 | Collagen Type I | MAP Kinase 13 | TIMP3 | Ryanodine receptor | EGFR | MUC1 |
|---|---|---|---|---|---|---|---|---|---|---|
| Caov-3 | 2.27 | 0.67 | 0.34 | 1.52 | 0.94 | n.d. | 1.00 | 0.26 | 1.27 | n.d. |
| SK-OV-3 | 1.86 | 0.29 | 0.69 | 0.72 | 1.32 | n.d. | 1.09 | 0.01 | 0.30 | n.d. |
| OVCAR-3 | 1.21 | 0.98 | 1.06 | 0.86 | 1.16 | n.d. | 1.54 | 0.46 | 0.13 | n.d. |
| TOV-21G | 0.77 | 1.50 | 0.79 | 0.92 | 1.50 | n.d. | 5.80 | 0.90 | 1.79 | n.d. |
| TOV-112D | 1.03 | 3.80 | 0.03 | 1.16 | 0.31 | n.d. | 5.00 | 1.57 | 1.50 | n.d. |

*n.d.—not detectable

Examples of Comparison of with Existing Technologies
Sodium Dodecyl Sulfate Polyacrylamide Gel Electrophoresis Protein concentration was determined using the bicinchoninic acid (BCA) assay (Pierce #23225, Thermo Scientific, Rockford, IL), according to the manufacturer's instructions. For sodium dodecyl sulfate (SDS)-PAGE, samples were denatured in in 6×SDS sample buffer (final concentrations: SDS10%, glycerol 10%, (3-mercaptoethanol 1%, bromophenol blue 0.004%, Tris-HCl 0.5 M, pH 6.8) and boiled for 5 minutes in a heating block. Samples (1-80 μg; Table 3) were loaded on gradient gels (4-12% bis-tris gels, 4% tris-glycine, or 3-8% tris acetate; Table 3; Invitrogen, Carlsbad, CA) and proteins separated electrophoretically in running buffer containing 3-(N-morpholino) propanesulfonic acid (MOPS) or tris acetate, respectively (both from Invitrogen, Carlsbad, CA) for 45 minutes at 20 mA. Recombinant protein was used to establish a standard curve if available (Table 5). Proteins were transferred onto a 0.2 μM nitrocellulose membrane (Pall Life Sciences, Ann Arbor, MI) in transfer buffer containing 25 mM Tris pH 8.6, 192 mM glycine, 0.1% SDS, 20% methanol for 1 hour at 900 mA. The membrane was blocked with 5% milk, 0.2% Tween-20 in PBS, or 0.5% casein/0.05% Tween-20 in PBS for 1 hour, incubated with primary antibody (Table 3) overnight at 4° C., washed three times with 2.5% milk/0.2% Tween-20 in PBS or PBS, and probed with secondary antibody (1:10,000 dilution; donkey anti-rabbit, or donkey anti-mouse obtained from GE Healthcare [Piscataway, NJ] or donkey anti-sheep [Sigma Aldrich, St. Louis, MO];) for 1 hour at ambient temperature. Immunoblots were developed using the Luminata Forte Western HRP substrate (Millipore, Billerica, MA), Western Lightning Plus or Western Lightning Ultra Chemoluminescence substrates (Perkin Elmer, Waltham, MA), or the Immun-Star WesternC kit (Biorad Laboratories, Hercules, CA). Membranes were imaged using film (Thermo Scientific, Rockford, IL) and processed on a Minolta film processor (Konica Minolta Medical Imaging USA, Inc., Wayne, NL).

TABLE 16

Immunoblotting conditions

| Target | Gel type and running buffer | Total protein loaded (μg) | Host | Dilution | Blocking solution | Developer |
|---|---|---|---|---|---|---|
| Fibronectin | 3-8% Tris-acetate TA buffer | 25 | Mouse | 1:1,000 | 0.5% Casein, 0.05% Tween-20 | Western Lightning Ultra |
| Apolipoprotein A1 | 4-12% Bis-Tris MOPS buffer | 40 | Mouse | 1:1,000 | 5% milk in PBS, 0.02% Tween-20 | Luminata Forte |

TABLE 16-continued

Immunoblotting conditions

| Target | Gel type and running buffer | Total protein loaded (μg) | Host | Dilution | Blocking solution | Developer |
|---|---|---|---|---|---|---|
| Calreticulin | 4-12% Bis-Tris MOPS buffer | 1 | Mouse | 1:7,000 | 0.5% Casein, 0.05% Tween-20 | Western Lightning Ultra |
| Collagen Type I | 4-12% Bis-Tris MOPS buffer | 25 | Sheep | 1:1,000 | 5% milk in PBS, 0.02% Tween-20 | Western Lightning Plus |
| Complement C7 | 4-12% Bis-Tris MOPS buffer | 25 | Rabbit | 1:1,000 | 5% milk in PBS, 0.02% Tween-20 | Luminata Forte |
| MAP Kinase 13 | 4-12% Bis-Tris MOPS buffer | 40 | Mouse | 1:1,000 | 5% milk in PBS, 0.02% Tween-20 | Immun-Star WesternC |
| TIMP 3 | 4-12% Bis-Tris MOPS buffer | 40 | Mouse | 1:1,000 | 5% milk in PBS, 0.02% Tween-20 | Immun-Star WesternC |
| Ryanodine receptor | 4% Tris-glycine | 80 | Rabbit | 1:10,000 | 20% donkey serum, 1% BSA | Immun-Star WesternC |

Densitometry and Statistical Analysis

Films were scanned using a commercial high-resolution scanner at 2,400-dpi resolution and converted to 12-bit grayscale TIFF files. Densitometry analysis was performed using Image J software (National Institute of Health, Bethesda, MD). Prism 5.01 software (GraphPad Software Inc., La Jolla, CA) was used for plotting and statistical analysis of the data. Table 16 lists the immunoblotting specific conditions for the eight biomarker array.

TABLE 17

Relative levels of protein release into supernatant compared to media control using Western blot analysis.

| Cell line | Fibronectin | Apolipoprotein A1 | Calreticulin | Complement C7 | Collagen Type I | MAP Kinase 13 | TIMP 3 | Ryanodine receptor |
|---|---|---|---|---|---|---|---|---|
| Caov-3 | 2.06 | 3.04 | 0.44 | 2.17 | 0.85 | n.d. | n.d. | n.d. |
| SK-OV-3 | 2.07 | 0.31 | 0.55 | 0.59 | 2.24 | n.d. | n.d. | 0.22 |
| OVCAR-3 | 1.14 | 1.06 | 1.27 | 0.52 | 1.10 | n.d. | n.d. | 1.14 |
| TOV-21G | 0.89 | 1.37 | 0.63 | 0.89 | 1.69 | n.d. | n.d. | 0.09 |
| TOV-112D | 1.07 | 1.42 | 0.08 | 1.31 | 0.98 | n.d. | n.d. | 0.00 |

As summarized in Table 17, relative protein release into the supernatant was calculated by performing densitometry on immunoblots and normalization for concentration. Release (as defined as >1.5-fold increase in protein in supernatant compared with media control) is highlighted in bold. Values larger than 1 suggest release; values smaller than 1 suggest uptake or degradation. n.d.=not detectable.

TABLE 18

Absolute protein levels (μg/mL) in media and supernatant using Western blot analysis.

| | Cell line | Fibronectin | Apolipoprotein A1 | Calreticulin | Collagen type I |
|---|---|---|---|---|---|
| Caov-3 | media | 0.45 | 0.01 | 52.14 | 0.59 |
| | supernatant | 0.93 | 0.02 | 22.79 | 0.50 |
| SK-OV-3 | media | 0.58 | 0.04 | 13.71 | 0.40 |
| | supernatant | 1.20 | 0.01 | 7.55 | 0.88 |

TABLE 18-continued

Absolute protein levels (μg/mL) in media and supernatant using Western blot analysis.

| Cell line | | Fibronectin | Apolipo-protein A1 | Calreticulin | Collagen type I |
|---|---|---|---|---|---|
| OVCAR-3 | media | 1.25 | 0.26 | 44.20 | 0.85 |
| | supernatant | 1.43 | 0.27 | 55.97 | 0.94 |
| TOV-21G | media | 0.86 | 0.02 | 39.65 | 0.69 |
| | supernatant | 0.77 | 0.03 | 25.04 | 1.16 |
| TOV-112D | media | 0.84 | 0.08 | 33.59 | 0.68 |
| | supernatant | 0.89 | 0.11 | 2.71 | 0.67 |

Table 18 describes absolute protein levels in cell supernatant and media control, determined using recombinant protein standards and densitometry analysis of immunoblots.

Comparison of Western Blot and GMR Detection System

For our proof-of-concept experiments, we compared absolute and relative protein levels of biomarkers for ovarian cancer in ovarian cancer cell lines of various cancer stages utilizing traditional quantitative Western blot analysis and the novel GMR detection system (summarized in FIGS. 32-36). Overall, we found a very high degree of agreement between the two technologies, confirming that the GMR detection system can provide accurate quantification of protein levels.

For instance, comparing the relative protein level of Fibronectin in both supernatants and media controls, we obtained highly comparable data that varied by less than ±15%, whereas the absolute protein determination varied by no more than ±25%. Similarly consistent data was obtained for all proteins tested.

It should be noted that the quantification using Western blot analysis is associated with very large intrinsic variation, which is a result of the multitude of experimental steps and readouts required including the initial assessment of protein quantification, loading of the SDS-PAGE gel, transfer efficiency, specificity of the antibodies, amplification of the signal using secondary antibodies, the linearity of the detection reagent, and the limited linear range of film. Taken together, this is likely the reason that we were unable to detect MAPK13 and TIMP3 protein in the supernatant of any cell line. Furthermore, variation for individual cell line samples is likely the result of the Western blot technology reaching the lower limit of detection sensitivity. For instance, for detection of Apolipoprotein A1, 40 μg total protein were loaded per well to obtain a very weak signal after prolonged exposure time of 5 minutes, reaching the maximum capacity of the wells without the need for concentration of the samples as well as the peak intensity of the chemoluminescence substrate. In contrast, the GMR detection system yielded reproducible datasets highlighting the sensitivity of the technology that far surpasses that of traditional Western blotting approaches.

All biomarker proteins were chosen based on initial genomic and proteomic data suggesting their up-regulation either in primary ovarian carcinoma or in late-stage advanced metastatic carcinoma. Therefore, we chose five cell lines representing various stages of ovarian cancer (see Table 2). Our data shows the differential release of the selected proteins in the various ovarian cancer cell lines, confirming their potential to serve as biomarkers for distinguishing primary versus metastatic ovarian cancer. Importantly, quantification of biomarker proteins was consistent between Western blot and the GMR detection system.

Fabrication of Sensor Arrays

FIG. 37 depicts a 50-micron spotted array fabricated by the inventors using biochemical spotting equipment (Sonoplot). A 10×10 sensor array is shown in the scanning electron microscope image. Each element is approximately 50 microns in diameter with 100 micron spacing. This microplotter may be utilized to define an antibody array on the biochip for a 100-channel (or more) biochip system.

Data Analysis and Backfitting Examples

Figure 38:
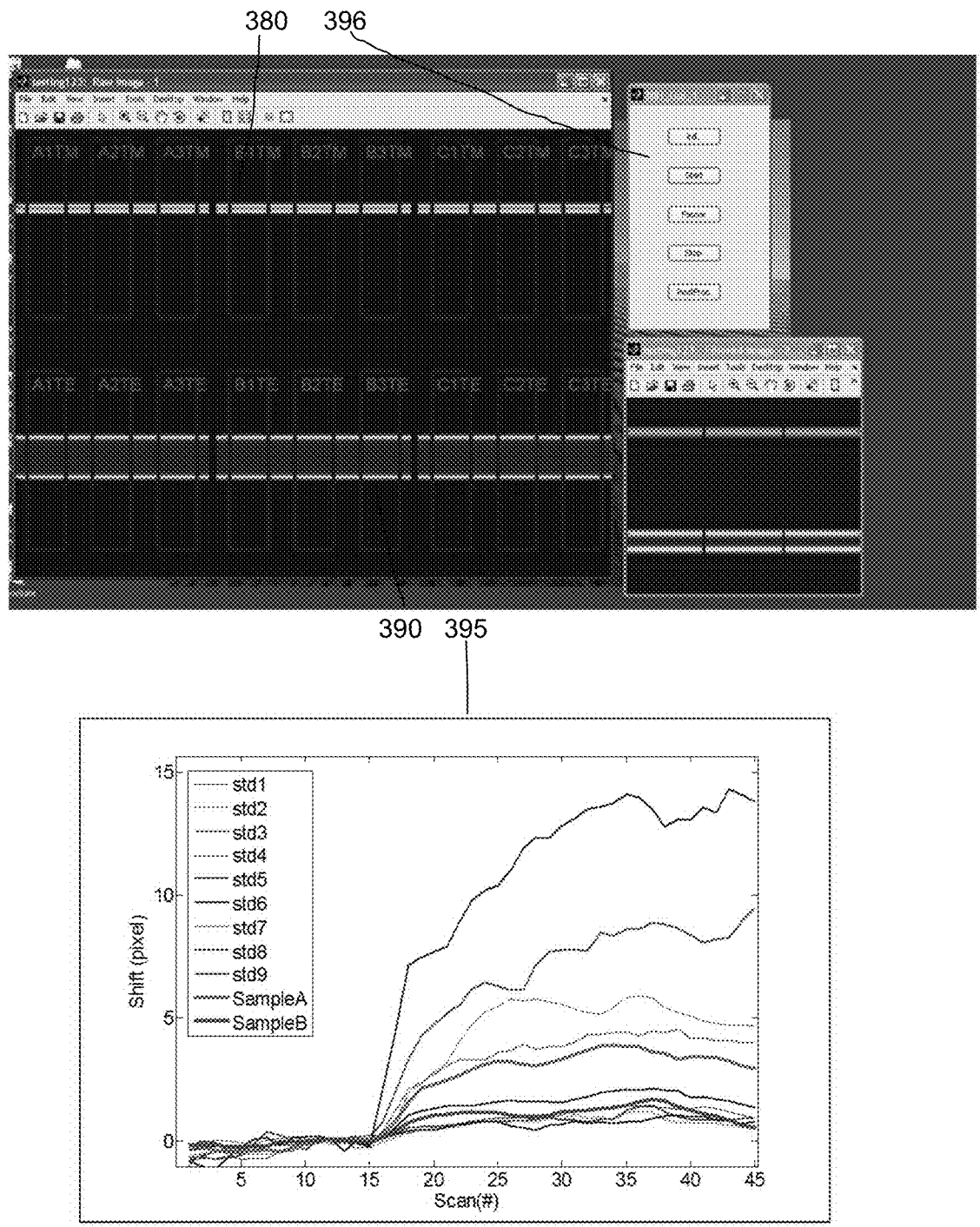
FIG. 38. Sensor system software output developed in this invention for the angular detection prototypes described in FIGS. 9-12. Both TE and TM resonance polarizations can be tracked for an eight-element sensor array. Resonance peak locations are tracked as relative shifts on the imager pixels versus time (or scan number).

A user interface has been developed in MATLAB to acquire the CCD or CMOS camera images from the angular setups shown in FIGS. 10-12, and to determine the resonance peak locations during an experiment. FIG. 38 shows a snapshot of the software program output developed and used to obtain resonance peak shift data for the angular system in this invention. The program is designed to track resonance peak changes on an eight-element array for both TE 390 and TM 380 polarization resonances. For each sensor element in the array, the raw image is filtered using a low-pass filter (MATLAB). The resonance peak location on the camera pixels is determined by peak-fitting algorithms, and the relative shifts are output to the user for analysis. A measured resonance peak shift as a function of time 395 (or scan number) is shown in the image inset. The data acquisition can be paused during detection 396 (as needed when dispensing the sample on the sensor element after a baseline is acquired).

To improve the detection accuracy of the biomolecular binding events, we monitor both polarization (TE and TM) peaks. This added layer of information greatly increases detection accuracy when a database of known binding characteristics for a particular material is provided. A GMR sensor layer that supports N modes in a given wavelength band exhibits N resonance peaks. We design the sensor to support the fundamental modes $TE_0$ and $TM_0$. Then, an unpolarized interrogating beam will generate corresponding separate resonance peaks. These resonance peaks shift in response to the reaction, providing two sets of data. By backfitting this dual-peak response into our rigorous electromagnetic coupled-wave analysis [40] codes, we can determine two unknowns. This powerful backfitting approach can be used to distinguish background index changes, such as those that might occur due to thermal or sample background changes, from attaching biolayers; this provides the ability to significantly reduce false positives and testing errors.

Figure 39:
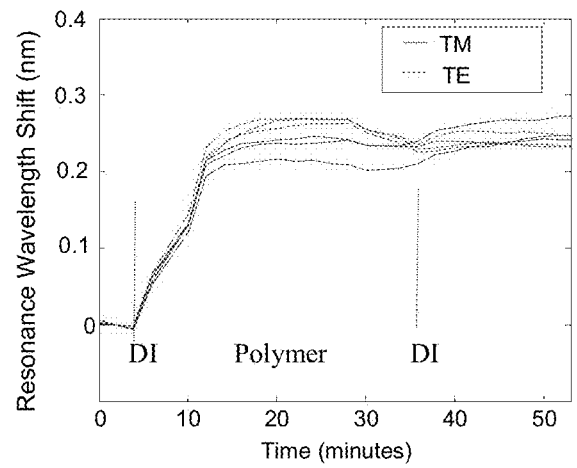
FIG. 39. Dual polarization resonance response for poly (allylamine hydrochloride) binding to the sensor showing resonance wavelength shift as a function of time. This medium has molecular weight of 56 kDa with a concentration of 1.3 mg/ml and pH 9.0.
Figure 40:
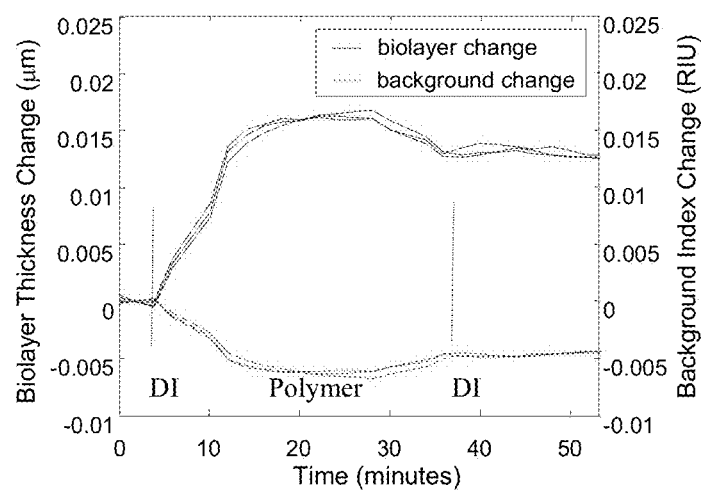
FIG. 40. Results of backfitting to a simple model, thereby differentiating contributions from biolayer adhesion and background changes. Thus, we estimate the final adhered layer thickness to be ~15 nm as noted by the scale on the left side of the figure.

As shown in FIGS. 1, 6 and 8, there are separate resonance peaks for each polarization (TE and TM) that shift in response to a given measurement, thus providing two sets of data. By backfitting this dual-peak response into our rigorous electromagnetic coupled wave analysis codes [17] we can determine two unknowns: surface changes due to accumulated biomaterial, and bulk refractive-index changes that might occur due to thermal variations or sample background changes. We first calculate and map the predicted TE and TM resonance peak shifts over a relevant range of added biolayer thicknesses (0 to 50 nm) and background index variations (n=1.33 to n=1.5). A simple matrix is applied to match the corresponding detection layer and background index when the two resonance peak shifts are known. This data is fitted assuming a known biolayer refractive index, with unknown values to be determined for the biolayer thicknesses and background index. Alternatively, the user could select to fit other parameters. To illustrate the utility of this approach, we use the ionic polymer poly (allylamine hydrochloride) [75,76] to study binding interactions that involve biolayer adhesion and associated thickness change at the sensor surface [17]. Two resonance peaks are tracked as the ionic polymer attaches a monolayer of material as shown in FIG. 39. After the polymer saturates, the measurement is paused and the sensor is washed to remove any unbound polymer. A post-binding measurement is made in DI water. The results in FIG. 40 show that the binding of the polymer layer to the sensor surface contributes most to the measured sensor response. The fitted background drift is partially attributed to thermal changes in the sample during the measurement and partly to imperfect model assumptions (such as polymer layer index). Improvements to the backfit model will further distinguish these contributions.

While the compositions and methods of this invention have been described in terms of specific embodiments, it will be apparent to those of skill in the art that variations may be applied to the compositions and/or methods and/or apparatus and in the steps or in the sequence of steps of the method described herein without departing from the concept, spirit and scope of the invention. For example, it is contemplated that additional and/or different biomarkers can be incorporated in order to detect (diagnose, screen or otherwise) a targeted disease, or improve upon disease detection accuracy, or detect multiple diseases. The array of biomarkers may be expanded to include genetic markers, or other new chemistries that become available. Additionally, the sensor detection system may be expanded to measure thousands of sensors in arrays and the hardware can be miniaturized to a highly compact form using the same basic components described herein.

What is claimed is:

1. A biomarker sensor measurement system, comprising:
a source of light,
a guided mode resonance (GMR) sensor assembly comprising a waveguide structure having disposed thereon an array of at least first, second and third biologically selective agents for selectively binding, respectively, to at least first, second and third biomarkers that are distinct from one another and which become part of the waveguide structure when bound and are measurably differently resonance-shifted from each other when bound and selected from the group consisting of: Fibronectin, Apolipoprotein A-1, Calreticulin, Complement C7, Collagen Type I, EGFR, MUC1 and Ryanodine receptor that may be present in media in contact with said waveguide structure, at least one of the first, second or third biomarkers being EGFR, and such that detection of said first, second and third biomarkers in predetermined combinations in said media is indicative of at least a first, or second disease state, said biologically selective agents being selected from the group consisting of antibodies, aptamers, peptides, DNA and RNA designed to be respectively selective or one of said first, second or third biomarkers;
at least said first and second biomarkers having an at least two-fold up-or down-regulation indicative of at least a first or second disease state, said third biomarker having an at least two-fold up-or down-regulation indicative of said second disease state, said up-or down-regulation of said third biomarker being opposite in up-or down-regulation sense from the up-or down-regulation of at least one of said first and second biomarkers in the presence of at least one of said first and second disease states, whereby said first and second disease states may be distinguished from each other, wherein said first or second disease states are primary or metastatic ovarian serous papillary carcinoma, respectively;
a beam shaper for receiving input light from a source of light, wherein said beam shaper includes one or more line focusing elements to focus input light onto the waveguide structure to cause one or more leaky transverse electrical light (TE) and transverse magnetic light (TM) resonant modes;
a light sensitive detector for detecting presence of said at least first, second and third biomarkers,
wherein the light sensitive detector is disposed with respect to said waveguide structure to detect changes in one or more of the angle, phase, waveshape and/or magnitude of each of a TE resonance and a TM resonance to permit distinguishing between first and second physical states of said waveguide structure or its immediate environment, said immediate environment including said media,
said light-sensitive detector having an output.

2. The measurement system of claim 1 where the source of light comprises multiple sources of light having distinct wavelengths.

3. The measurement system of claim 1, wherein the Ryanodine receptor is Ryanodine receptor 2 or Ryanodine receptor 3.

4. The measurement system of claim 1, further comprising at least a fourth biologically selective agent for selectively binding, respectively, to at least one other biomarker selected from the group consisting of: Fibronectin, Apolipoprotein A-1, Calreticulin, Complement C7, Collagen Type I, EGFR, MUC1 and Ryanodine receptor that may be present in media in contact with said waveguide structure, at least one of which biomarkers is EGFR, said fourth biologically selective agent being distinct from said first, second and third biologically selective agents and being selective for at least one other biomarker protein that becomes part of the waveguide structure when bound and is measurably differently resonance-shifted from the other biomarker proteins when bound and up-or down-regulated at least two-fold in at least one ovarian cancer disease state, wherein said disease state is an ovarian cancer disease stage.

5. The measurement system of claim 1, said at least first, second and third biomarkers are associated with at least a first or second disease state of ovarian cancer.

6. The measurement system of claim 1, wherein said at least first, second and third biomarkers are associated with different states of ovarian cancer treatment efficacy.

7. The measurement system of claim 6, wherein said different states of ovarian cancer treatment efficacy are respectively predictive of the likely success of respectively different ovarian cancer treatment modalities.

8. The measurement system of claim 1, wherein said media in contact with said waveguide structure includes a fluid taken from the group consisting of: serum, blood, urine and other biological fluids obtained from a clinical sample.

9. The measurement system of claim 1, wherein the light sensitive detector is powered using a USB port interface from a computer and/or an on-board battery, and wherein the system is powered using a USB port interface from a computer and/or an on-board battery.

10. The measurement system of claim 1, wherein the first of said at least first, second and third biologically selective agents selectively binds to Complement C7, and said second and third of said at least first, second and third biologically selective agents bind to, respectively, at least two proteins selected from the group consisting of: Fibronectin, Apolipoprotein A-1, Calreticulin, Collagen Type I, EGFR, MUC1 and Ryanodine receptor.

11. The measurement system of claim 1, wherein at least one combination of a set of predetermined combinations of said at least three biomarker proteins is associated with the presence of a third disease state of a lack of primary and metastatic ovarian serous papillary carcinoma.

12. A GMR biosensor for detecting the presence of ovarian cancer biomarker proteins in a sample, comprising:
a GMR sensor assembly having a waveguide structure having disposed thereon an array of at least first, second and third biologically selective agents for selectively binding, respectively, to at least first, second and third biomarker proteins that become part of the waveguide structure when bound and are distinct from one another and measurably differently resonance-shifted from each other when bound and selected from the group consisting of: Fibronectin, Apolipoprotein A-1, Calreticulin, Complement C7, Collagen Type I, EGFR, MUC1 and Ryanodine receptor that may be present in media in contact with said waveguide structure, at least one of the first, second and third biomarker proteins being EGFR, and such that detection of said first, second and third biomarker proteins in predetermined combinations in said media in contact with said waveguide structure is indicative of at least a first or second disease state, said biologically selective agents being selected from the group consisting of antibodies, aptamers, peptides, DNA and RNA designed to be respectively selective for one of said first, second or third biomarker proteins;
said waveguide structure being configured for operation at or operably near one or more leaky modes before and after said first, second and third biomarker proteins bind to, respectively, said at least first, second and third biologically selective agents,
a beam shaper for receiving input light from a source of light that includes one or more line focusing elements to focus input light onto the waveguide structure to cause one or more leaky TE and TM resonant modes;
a light sensitive detector for detecting, in media in contact with said waveguide structure, presence of at least said first, second and third biomarker proteins indicative of said first and second disease states, wherein said first and second disease states are primary or metastatic ovarian serous papillary carcinoma, comprising means for detecting changes in one or more of the angle, phase, waveshape and/or magnitude of either or both of a TE resonance and a TM resonance to permit distinguishing between first and second physical states of said waveguide structure or its immediate environment, said immediate environment including said media, wherein said least two of said first, second and third protein biomarkers have an at-least two-fold up-or-down regulation indicative of at least said first disease state of primary or metastatic ovarian serous papillary carcinoma, respectively,
said third of said, first, second and third protein biomarkers having an at least two-fold up-or-down regulation indicative of a disease state, said up-or down-regulation of said third biomarker being significantly statistically different from the up-or-down regulation of at least one of said first and second protein biomarkers in the presence of at least one of said first and second disease states,
said light-sensitive detector having an output.

13. The GMR biosensor of claim 12, wherein the Ryanodine receptor is Ryanodine receptor 2 or Ryanodine receptor 3.

14. The GMR biosensor of claim 12, wherein said at least first, second and third biomarker proteins are associated with at least a first or second disease state of ovarian cancer.

15. The GMR biosensor of claim 12, wherein said at least first, second and third biomarker proteins are associated with different states of ovarian cancer treatment efficacy.

16. The GMR biosensor of claim 12, wherein said media in contact with said waveguide structure includes a fluid taken from the group consisting of: serum, blood, urine and other biological fluids obtained from a clinical sample.

17. The GMR biosensor of claim 12, wherein the GMR biosensor utilizes a guided-mode resonance waveguide grating to detect the presence of the ovarian cancer biomarker proteins.

18. The GMR biosensor of claim 12, wherein said GMR biosensor including means for determining which one of a set of predetermined combinations of said at least three biomarker proteins are present, at least one of said combinations being correlated to a cell's phenotype of disease states of ovarian cancer.

19. The GMR biosensor of claim 12, wherein the GMR biosensor has different sets of said at least first, second and third biomarker proteins that are distinct from one another are associated with the respective presence of primary as distinguished from metastatic ovarian serous papillary carcinoma.

* * * * *